United States Patent
Hartwig et al.

(10) Patent No.: US 9,758,453 B2
(45) Date of Patent: Sep. 12, 2017

(54) ONE-COMPONENT REAGENT FOR THE FLUOROALKYLATION REACTION

(71) Applicant: The Board of Trustees of the University of Illinois, Urbana, IL (US)

(72) Inventors: John F. Hartwig, Champaign, IL (US); Hiroyuki Morimoto, Higashi-ku (JP); Patrick Fier, Berkeley, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/919,557

(22) Filed: Oct. 21, 2015

(65) Prior Publication Data

US 2016/0185691 A1 Jun. 30, 2016

Related U.S. Application Data

(60) Division of application No. 13/770,430, filed on Feb. 19, 2013, now Pat. No. 9,193,648, which is a
(Continued)

(51) Int. Cl.
*B01J 31/18* (2006.01)
*C07C 17/32* (2006.01)
(Continued)

(52) U.S. Cl.
CPC ........... *C07C 17/32* (2013.01); *B01J 31/0231* (2013.01); *B01J 31/0235* (2013.01); *B01J 31/0244* (2013.01); *C07B 39/00* (2013.01); *C07C 17/263* (2013.01); *C07C 29/32* (2013.01); *C07C 37/11* (2013.01); *C07C 41/30* (2013.01); *C07C 41/48* (2013.01); *C07C 45/63* (2013.01); *C07C 45/68* (2013.01); *C07C 67/293* (2013.01); *C07C 67/343* (2013.01); *C07C 201/12* (2013.01); *C07C 209/68* (2013.01); *C07C 231/12* (2013.01); *C07C 253/30* (2013.01);
(Continued)

(58) Field of Classification Search
CPC ....... C07B 39/00; C07C 17/263; C07C 17/32; C07C 201/12; C07C 209/68; C07C 231/12; C07C 253/30; C07C 29/32; C07C 37/11; C07C 41/30; C07C 41/48; C07C 45/63; C07C 45/68; C07C 67/293; C07C 67/343; C07D 209/08; C07D 209/10; C07D 213/26; C07D 213/61
See application file for complete search history.

(56) References Cited

U.S. PATENT DOCUMENTS 5,670,679 A 9/1997 Baker et al.
6,410,796 B2 6/2002 Kuhnle et al.

FOREIGN PATENT DOCUMENTS

EP 1151987 11/2001
WO 04000764 12/2003

OTHER PUBLICATIONS

Krylova, V. A. et al. Chem. Comm. 2010, 46, pp. 6696-6698; Published Aug. 17, 2010.*
(Continued)

Primary Examiner — Medhanit Bahta
(74) Attorney, Agent, or Firm — Pitts & Lake, P.C.

(57) ABSTRACT

A composition, consisting essentially of copper, a fluoroalkyl group, and a ligand comprising at least one group-V donor. The molar ratio of copper to the fluoroalkyl group is approximately 1.

7 Claims, 5 Drawing Sheets

Related U.S. Application Data continuation of application No. PCT/US2011/048378, filed on Aug. 19, 2011.

(60) Provisional application No. 61/375,396, filed on Aug. 20, 2010.

(51) Int. Cl.

| | | |
|---|---|---|
| *B01J 31/02* | (2006.01) | |
| *C07B 39/00* | (2006.01) | |
| *C07C 17/263* | (2006.01) | |
| *C07C 29/32* | (2006.01) | |
| *C07C 41/30* | (2006.01) | |
| *C07C 41/48* | (2006.01) | |
| *C07C 45/68* | (2006.01) | |
| *C07C 67/293* | (2006.01) | |
| *C07C 67/343* | (2006.01) | |
| *C07C 201/12* | (2006.01) | |
| *C07C 209/68* | (2006.01) | |
| *C07C 231/12* | (2006.01) | |
| *C07C 253/30* | (2006.01) | |
| *C07D 209/10* | (2006.01) | |
| *C07D 213/26* | (2006.01) | |
| *C07D 215/18* | (2006.01) | |
| *C07D 239/54* | (2006.01) | |
| *C07F 1/08* | (2006.01) | |
| *C07C 37/11* | (2006.01) | |
| *C07C 45/63* | (2006.01) | |
| *C07D 209/08* | (2006.01) | |
| *C07D 213/61* | (2006.01) | |
| *C07D 239/22* | (2006.01) | |
| *C07D 215/12* | (2006.01) | |
| *C07C 22/08* | (2006.01) | |

(52) U.S. Cl.
CPC ......... *C07D 209/08* (2013.01); *C07D 209/10* (2013.01); *C07D 213/26* (2013.01); *C07D 213/61* (2013.01); *C07D 215/12* (2013.01); *C07D 215/18* (2013.01); *C07D 239/22* (2013.01); *C07D 239/54* (2013.01); *C07F 1/08* (2013.01); *C07C 22/08* (2013.01)

(56) References Cited

OTHER PUBLICATIONS

Chavan, S. S. et al. Inorg. Chim. Acta. 2010, 363, pp. 3359-3364; Published Jun. 22, 2010.*

Nishat, N. et al. Synth. React. Inorg. Metal-Org. Chem. 2004, 34, pp. 335-351.*

Usui, Y. et al. "C—Si bond cleavage of trihalomethyltrimethylsilane by alkoxo- and aryloxogold or -copper complexes" Inorganica Chimica Acta 309 (2000) 151-154.*

Nair, H. K. et al. "Formation of group 11 trifluoromethyl derivatives by reaction of Cd(CF3)2•glyme with representative gold, silver, and copper complexes: isolation of Au(CF3)3(PMe3), Au(CF3)3(PEt3), AuI(CF3)3(PMe3), AuCF3(PMe3), AuCF3(PEt3) and AgCF3(PMe3); observation of CuCF3(PMe3)" J. Organometallic Chem. 1989, 376, pp. 149-164; Abstract Only.*

International Searching Authority, "International Search Report and Written Opinion for PCT/US2011/48378", Jan. 10, 2012, Publisher; European Patent Office.

Ackerman et al., "Tetra-Ortho-Substituted Biaryls through Palladium-Catalyzed Suzuki-Miyaura Couplings with a Diaminochlorophosphine Ligand", 2010, pp. 1004-1007, vol. 12, No. 5, Publisher: Organic Letters.

Arisawa et al., "Rhodium-Catalyzed Methylthio Transfer Reaction between Ketone r-Positions: Reversible Single-Bond Metathesis of C—S and C—H Bonds", 2009, pp. 625-627, vol. 11, No. 3, Publisher: Organic Letters.

Bjornestedt et al., "Copying Natures Mechanism for the Decarboxylation of-Keto Acids Into Catalytic Antibodies by Reactive Immunization", 1996, pp. 11720-11724, vol. 118, Publisher: Journal of American Chemical Society.

Chen et al., "Methyl Fluorosulphonyldifluoroacetate; a New Trifluoromethylating Agent", 1989, pp. 705-706, Publisher: Journal of the Chemical Society, Chemical Communications.

Cho et al., "The Palladium-Catalyzed Trifluoromethylation of Aryl Chlorides", Jun. 25, 2010, pp. 1679-1681, vol. 328.

Cottet et al., "Trifluorornethyl-Substituted Pyridines Through Displacement of Iodine by in situ Generated (Trifluormethyl) copper", 2002, pp. 327-330, Publisher: European Journal of Organic Chemistry.

Defrees et al., "A Selective and Efficient Method for the Deprotection of N-Benzyloxymethyl (BOM) Protecting Groups from Pyrimidine and Dihydropyrimidine Ring Systems", 1988, pp. 213-220, vol. 18, No. 2, Publisher: Synthetic Communications, Published in: West Lafayette, IN.

Dubinina et al., "Structure of Bis(trifluoromethypcuprate and its Role in Trifluoromethylation Reactions", 2008, p. 6233-6235, vol. 27, No. 23, Publisher: Organometallics.

Fialkov et al., "Fluorine-Containing Liquid Crystals. VIII. 4-Perfluoroalkyl-4'-Alkylaminobiphenyls", May 1983, pp. 932-937, vol. 19, No. 5, Publisher: Journal of Organic Chemistry of the USSR.

Furuya et al., "Silver-Mediated Fluorination of Functionalized Aryl Stannanes", 2009, pp. 1662-1663, vol. 131, No. 5, Publisher: Journal of American Chemistry Society.

Iwanaga et al., "Study on the Electronic Effect on Coordinating Donors in Heptacoordinate Trichlorogermanes", Page(s).

Kutt et al. "Pentakis (trifluormethyl)phenyl, a Sterically Crowded and Electron-Withdrawing Group: Synthesis and Acidity of Peritakis(trifluormethyl)benzene,-toluene, -phenol, and-aniline", 2008, 2607-2620,vol. 73, Publisher: Journal of Organic Chemistry.

Lemmen et al., "Alcohol Elimination Chemistry of (CUOBU)", 1990, pp. 3680-3685, vol. 29, No. 19, Publisher: Organic Chemistry.

Lin et al., "Highly Functionalized Benzene Syntheses by Directed Mono or Multiple Magnesiations with TMPMgClLiCl", 2006, pp. 5673-5676, vol. 8, No. 24, Publisher: Organic Letters.

Milburn et al., "3,3'-Dipyridyl BINOL Ligands. Synthesis and Application in Enantioselective Addition of Et2Zn to Aldehydes#", 2007, pp. 4403-4406, vol. 9, No. 22, Publisher: Organic Letters.

Molander et al., "Reductive Radical Cyclizations of Haloalkenes Promoted by Samarium Sequential Cyclization/Intermoleculr Carbonyl Addition Reactions", Mar. 12, 1990, pp. 6171-6176, vol. 55, No. 25, Publisher: Journal of Organic Chemistry.

Monnreau et al., "A Cheap and Efficient Method for Selective Para-Iodination of Aniline Derivatives", 2005, pp. 5421-5423, vol. 46.

O'Connor et al., "Susbstituent Effects on the N.M.R. Spectra of Carboxylic Acid Derivatives, III Correlation of 13C N.M.R. Spectra of Para Substituted Acetanilides and 4'-Nitrophenyl 4-Substituted Bonzoates with Infrared Carbonyl Stretching Frequencies . . . ", 1984, pp. 497-510, vol. 37, Publisher: Australian Journal of Chemistry.

Pratt et al., "Oxygen-Carbon Bond Dissociation Enthalpies of Benzyl Phenyl ethers and Anisoles. An Example of Temperature Dependent Substituent Effects 1", 2001, pp. 5518-5526, vol. 123, Publisher: Journal of American Cancer Society.

Shang et al, "Synthesis of Aromatic Esters via Pd-Catayzed Decarboxylative Coupling of Potassium Oxalate Monoesters with Aryl Bromides and Chlorides", 2009, pp. 5738-5739, vol. 131, Publisher: Journal of American Chemical Society.

Tsuda et al., "Cuprous tent-Butoxide. A New and Useful Metalation Reagent", Jan. 26, 1972, pp. 658-659, vol. 94, No. 2, Publisher: Journal of the American Chemical Society.

Urata, Hisao et al., "A Novel and Convenient Method for Trifluoromethylation of Organic Halide Using C3SIR3/KF/Cu(I)System", 1991, pp. 91-94, vol. 32, No. 1, Publisher: Tetrahedron Letters.

(56) References Cited

OTHER PUBLICATIONS

Wiemers, Denise M., et al., Pregeneration, Spectroscopic Detection, and Chemical Reactivity of (Trifluoromethyl) copper, an Elusive and Complex Species, 1986, Page(s) vol. 108, No. 4, Publisher: Journal of American Chemical Society.

Wu et al., "Assymetric Allylboration of Aldehydes and Ketones Using 3,3'-Disubstitutedbinaphthol-Modified Boronates", 2004, pp. 2701-2704, vol. 6, No. 16, Publisher: Organic Letters.

* cited by examiner

R = H (4a): 88%
R = *n*Bu (4b): 88% (83%)[b]
R = OMe (4c): 86%
R = NMe$_2$ (4d): 88%
R = Br (4e): 92%
R = CH$_2$OH (4f): 75%
R = COCH$_3$ (4g): 87%
R = CHO (4h): 92%
R = CN (4i): 92%
R = NO$_2$ (4j): 92%

R = Me (4k): 88%
R = OMe (4l): 90%
R = Cl (4m): 89%

R = Me (4n): 87%
R = OMe (4o): 96%

4p: 92%

ONE-COMPONENT REAGENT FOR THE FLUOROALKYLATION REACTION

REFERENCE TO RELATED APPLICATIONS

This application is a divisional of U.S. patent application Ser. No. 13/770,430 entitled "Fluoroalkylation Methods And Reagents" filed Feb. 2, 2013, which is a continuation of PCT Application No. PCT/US2011/048378 entitled "Fluoroalkylation Methods And Reagents" filed Aug. 19, 2011, which claims the benefit of U.S. Provisional Application No. 61/375,396 entitled "Fluoroalkylation Methods And Reagents" filed Aug. 20, 2010, each of which is incorporated by reference in its entirety.

FEDERALLY SPONSORED RESEARCH OR DEVELOPMENT

This invention was made with government support under Contract Number GM-58108 awarded by the National Institutes of Health. The Government has certain rights in the invention.

BACKGROUND

Fluoroalkyl substituents have become increasingly important in the research and development of biologically active compounds including pharmaceuticals. A number of existing blockbuster pharmaceuticals include a fluoroalkyl substituent. Incorporation of a trifluoromethyl group into an organic molecule can favorably change its lipophilicity and pharmacokinetics. In addition, investigations of an analogue of a compound in which a methyl group has been replaced by a trifluoromethyl group can provide insights into the biological activity of the compound.

Although the effect of the trifluoromethyl substituent on biological activity and pharmacokinetics has been studied, methods to incorporate the trifluoromethyl group into aromatic compounds are limited. Conventionally, aryl compounds have been substituted with trifluoromethyl groups through the reaction of aryl carboxylic acids with $SF_4$, or through the fluorination of a trichloromethyl substituent of an aryl compound with Swart's reagent ($SbF_3$). The $SF_4$ and $SbF_3$ reagents, however, are toxic and difficult to handle.

In another approach, trifluoromethyl groups have been incorporated into aromatic compounds using palladium-mediated or palladium-catalyzed reactions. Each of these approaches, however, has at least one disadvantage, such as limited toleration of functionality, high loadings of an expensive phosphine ligand, high loadings of palladium, high temperature conditions, or the need for an expensive $CF_3$ source.

In yet another approach, trifluoromethyl groups have been incorporated into aromatic compounds using copper(I) reagents and catalysts. These reactions, however, also have severe limitations for synthetic applications. Reactions of a trifluoromethylcopper complex prepared from CuX and either $Cd(CF_3)X$ or $Zn(CF_3)X$ have been reported, as have reactions using CuI and trialkyl(trifluoromethyl)silanes with KF as an activator. These methods, however, involve toxic cadmium reagents and HMPA solvent to facilitate formation of $CuCF_3$, and/or occur with limited functional group compatibility and in poor yields with electron-rich aryl halides. Trifluoromethylcopper compounds ligated by N-heterocyclic carbenes (NHC) are not useful for preparative work because the compounds are prepared by a three-step synthesis starting with an expensive NHC ligand. Trifluoromethylation catalyzed by copper iodide using methyl fluorosulfonyldifluoroacetate $FSO_2CF_2CO_2Me$ as the source of $CF_3$ generates toxic $SO_2$ and MeI and cannot be extended to higher perfluoroalkyl groups. Trifluoromethylation of aryl iodides with a catalytic amount of copper iodide ligated by 1,10-phenanthroline requires the expensive $TESCF_3$ reagent, and high yields were obtained only with electron-deficient aromatic halides.

Accordingly, it would be desirable to form fluoroalkylarenes under mild conditions in a manner that would tolerate a wide variety of functional groups. Preferably such a fluoroalkylation method would utilize reagents that are readily accessible, relatively inexpensive, and less toxic than conventional fluoroalkylation reagents.

SUMMARY

In one aspect, the invention provides a method of forming a fluorinated molecular entity that includes reacting in a reaction mixture an aromatic halide, copper, a fluoroalkyl group, and a ligand. The aromatic halide includes an aromatic group and a halogen substituent bonded to the aromatic group. The ligand includes at least one group-V donor selected from phosphorus and nitrogen. The overall molar ratio of copper to aromatic halide in the reaction mixture is from 0.2 to 3. The method further includes forming a fluoroalkylarene including the aromatic group and the fluoroalkyl group bonded to the aromatic group.

In another aspect of the invention, there is a composition consisting essentially of copper, a fluoroalkyl group, and a ligand including at least one group-V donor. The molar ratio of copper to the fluoroalkyl group is approximately 1.

In another aspect of the invention, there is a composition consisting essentially of copper, a fluoroalkyl group, a first ligand including at least one group-V donor, and a second ligand, different from the first ligand. The molar ratio of copper to the fluoroalkyl group is approximately 1.

In another aspect of the invention, there is a method of forming a fluorinated molecular entity that includes reacting in a reaction mixture a vinyl halide, copper, a fluoroalkyl group, and a ligand. The vinyl halide includes an organic group containing a vinyl group and a halogen substituent bonded to a carbon of the vinyl group. The ligand includes at least one group-V donor selected from phosphorus and nitrogen. The overall molar ratio of copper to vinyl halide in the reaction mixture is from 0.2 to 3. The method further includes forming a fluoroalkylvinyl compound including the organic group containing a vinyl group, and the fluoroalkyl group bonded to a carbon of the vinyl group.

In another aspect of the invention, there is a method of forming a copper-containing reagent that includes reacting in a reaction mixture a copper source, an alcohol, a compound including at least one group-V donor, and a tri-organo (fluoroalkylsilane). The copper source includes a copper-carbon bond or a copper-nitrogen bond. The method further Includes forming $[(L)Cu-R_f]$ in the reaction mixture; where L is a ligand comprising at least one group-V donor, and $R_f$ is a fluoroalkyl group.

To provide a clear and more consistent understanding of the specification and claims of this application, the following definitions are provided.

The term "molecular entity" means any constitutionally or isotopically distinct atom, molecule, ion, ion pair, radical, radical ion, complex, conformer etc., identifiable as a separately distinguishable entity.

The term "group" means a linked collection of atoms or a single atom within a molecular entity. The description of a group as being "formed by" a particular chemical transformation does not imply that this chemical transformation is involved in making the molecular entity that includes the group.

The term "chemical transformation" means the conversion of a substance into a product, irrespective of reagents or mechanisms involved.

The term "aromatic halide" means a molecular entity containing an aromatic group having a halide substituent (F, Cl, Br, I) bonded to the aromatic group.

The term "aromatic group" means a cyclic group containing an aryl group and/or a heteroaryl group. An aromatic group may be monocyclic or polycyclic and may include one or more substituent groups.

The term "aryl group" means a group formed by removing a hydrogen from a ring carbon atom of an aromatic hydrocarbon. An aryl group may be monocyclic or polycyclic and may include one or more substituent groups.

The term "heteroaryl group" means a group formed by replacing one or more methine (—C═) and/or vinylene (—CH═CH—) groups in an aryl group with a trivalent or divalent heteroatom, respectively. A heteroaryl group may be monocyclic or polycyclic and may include one or more substituent groups.

The term "substituent" means a group that replaces one or more hydrogen atoms in a molecular entity. Examples of substituents include halide groups, alkyl groups, heteroalkyl groups, aryl groups, and heteroaryl groups. A heteroalkyl or heteroaryl substituent may be bonded to the remainder of the molecular entity through a carbon or through a heteroatom.

The term "alkyl group" means a group formed by removing a hydrogen from a carbon of an alkane, where an alkane is an acyclic or cyclic compound consisting entirely of hydrogen atoms and saturated carbon atoms. An alkyl group may be substituted with one or more substituent groups.

The term "fluoroalkyl group" means an alkyl group substituted with one or more fluoride groups.

The term "ligand", when referring to a distinct substance, means an organic compound that can be associated to a metal atom when combined with the metal atom.

The term "group-V donor" means an atom from group-V of the periodic table (N, P, As, Sb), where the group-V atom is a Lewis base.

The term "group-VI donor" means an atom from group-VI of the periodic table (O, S, Se), where the group-VI atom is a Lewis base.

The term "heterocyclic group" means a group formed by removing a hydrogen from a carbon of a heterocycle, where a heterocycle is a cyclic compound consisting of hydrogen atoms, carbon atoms, and one or more heteroatoms. A heterocyclic group may include one or more substituent groups. Heterocyclic groups include cyclic heteroalkyl groups, cyclic heteroalkenyl groups, cyclic heteroalkynyl groups and heteroaryl groups.

The term "overall molar ratio" means the molar ratio of the total amounts of two reactants in a reaction mixture over the course of a reaction, which begins with the combination of at least a portion of the two reactants and ends when the yield of the product of the reaction is no longer increasing.

The term "fluoroalkylarene" means a molecular entity containing an aromatic group and a fluoroalkyl substituent bonded to the aromatic group.

The term "fluoroalkylvinyl compound" means a molecular entity containing an organic group that includes a vinyl group, and a fluoroalkyl substituent bonded to a carbon of the vinyl group.

The term "functional group" means a group that includes atoms other than hydrogen and $sp^3$ carbon atoms, and that has similar chemical properties when it occurs in different organic compounds. Examples of functional groups include hydroxyl (—OH), protected hydroxyl, ether (—C—O—C—), ketone (>C═O), ester (—C(═O)O—C—), carboxylic acid (—C(═O)OH), cyano (—C≡N), amido (—C(═O)NH—C—), protected amino, thiol (—SH), sulfone, sulfoxide, phosphine, phosphite, phosphate, and halide (—X).

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

Figure 1:
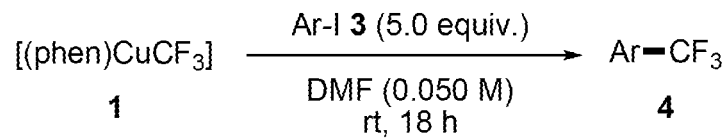
FIG. 1 depicts chemical structures, reaction schemes and product yields for examples of fluoroalkylation reactions of aromatic iodides.
Figure 1:
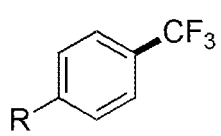
Figure 1:
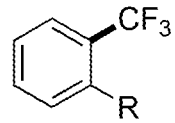
Figure 1:
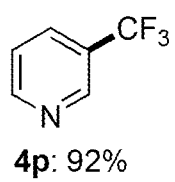

Fluoroalkylation may be performed with a range of organic halides by reacting an organic halide in a reaction mixture containing copper, a fluoroalkyl group, and an inexpensive ligand, where the overall molar ratio of copper to organic halide in the reaction mixture is from 0.2 to 3. The fluoroalkylation reaction may be carried out at room temperature, and may be effective with aromatic halides having substituents that are electron-donating, neutral or electron-withdrawing. A variety of fluoroalkyl groups can be used to replace the halide on the organic group.

Moreover, a composition containing the copper, the fluoroalkyl group and the ligand can serve as a shelf-stable, one-component reagent for the fluoroalkylation reaction. The reagent may be prepared from relatively inexpensive components, and may be stored at ambient temperature under a nitrogen atmosphere. The reagent may be used in a reaction mixture to provide fluoroalkylation of a range of organic halides.

A method of forming a fluorinated molecular entity includes reacting in a reaction mixture an aromatic halide, copper, a fluoroalkyl group and a ligand, and forming a fluoroalkylarene in the reaction mixture. The aromatic halide includes an aromatic group and a halogen substituent bonded to the aromatic group. The ligand includes at least one group-V donor. The overall molar ratio of copper to aromatic halide in the reaction mixture is from 0.5 to 3. The fluoroalkylarene formed in the reaction mixture includes the aromatic group and the fluoroalkyl group bonded to the aromatic group.

The aromatic halide includes an aromatic group and a halogen substituent bonded to the aromatic group. The halogen substituent preferably is bromine (—Br) or iodine (—I). The aromatic group may be an aryl group, and preferably may be any C6-C20 aryl group. Examples of aryl groups include a phenyl group, a biphenyl group and a binaphthyl group. The aromatic group may be a heteroaryl group, and preferably may be any C3-C20 heteroaryl group. Examples of heteroaryl groups include a pyridyl group, a quinoline group, a pyrimidine group and an indole group. The aromatic group may further include other substituents, such as an alkyl group, an ether group, a hydroxyl group, an aldehyde group, a ketone group, an ester group, an amine group, an amide group, a cyano group, a nitro group, a bromide group, and a chloride group. The aromatic halide may be electron-neutral, electron-rich or electron-deficient.

The copper preferably is present in the reaction mixture as copper(I). The copper may be present in the reaction mixture in any of a variety of forms, including an ion, a salt, a complex or a compound. The copper may be added to the reaction mixture as a complex with the fluoroalkyl group and/or the ligand. The copper may be added to the reaction mixture as a halide, such as copper(I) chloride (CuCl), copper(I) bromide (CuBr) or copper(I) iodide (CuI). The copper may be added to the reaction mixture as an oxide, such as copper(I) oxide ($Cu_2O$). The copper may be added to the reaction mixture as a complex with one or more alkoxy ligands, such as copper(I) t-butoxide [Cu—O-t-Butyl]$_4$. The copper may be added to the reaction mixture as a complex with one or more other ligands, such as copper(I) triflate or copper(I) thiocyanate.

The fluoroalkyl group preferably has the formula —$C_xH_{(2x-y)}F_y$, where x is from 1 to 12 and y is from 1 to (2x+1). Preferred fluoroalkyl groups include —$CF_3$, —$CF_2CF_3$, —$CH_2CF_3$, —$CH_2CH_2F$, —$CF_2CF_2CF_3$, —$CH_2CF_2CF_3$, —$CH_2CH_2CF_3$, —$CH_2CH_2CH_2F$, —$CH(CF_3)_2$ and —$CF(CF_3)_2$. The fluoroalkyl group may be added to the reaction mixture as part of a complex with the copper. The fluoroalkyl group may be added to the reaction mixture as part of a silane compound, such as a tri-organo(fluoroalkylsilane). Examples of tri-organo(fluoroalkylsilanes) include trimethyl (fluoroalkylsilanes), triethyl(fluoroalkylsilanes), dimethylphenyl(fluoroalkylsilanes), tert-butyl-dimethyl(fluoroalkylsilanes), tri isopropyl(fluoroalkylsilanes), trifluoromethyl (fluoroalkylsilanes), triphenylsilyl(fluoroalkylsilanes), tri-organo(perfluoroethylsilanes), tri-organo (perfluoropropylsilanes), and tri-organo(fluoroalkylsilanes) in which the fluoroalkyl group is partially fluorinated. For example, the fluoroalkyl group may be added as a trimethyl (fluoroalkylsilane) (TMS-$R_f$, where TMS denotes the trimethylsilyl group, and $R_f$ denotes the fluoroalkyl group). Specific examples of a trimethyl(fluoroalkylsilane) include trimethyl(trifluoromethylsilane) (TMS-$CF_3$, Ruppert's reagent). The fluoroalkyl group may be added to the reaction mixture as trifluoroacetic acid or methyl fluorosulfonyldifluoroacetate.

The ligand includes at least one group-V donor. Preferably the ligand includes at least one group-V atom such as phosphorus or nitrogen. More preferably the ligand includes at least one group-V atom selected from the group consisting of phosphorus, a ring nitrogen of a heterocyclic group, and an amine. The ligand may be added to the reaction mixture as part of a complex with the copper. The ligand may be added to the reaction mixture as a free compound, or it may be added as part of another substance, such as a salt of the ligand with an ion or a complex of the ligand with another metal.

Examples of ligands that include at least one phosphorus atom, a ring nitrogen of a heterocyclic group, or an amine include a phenanthroline, an N,N'-disubstituted diamine, a bipyridyl, a pyridyl, a phosphine, and a phosphite. Each of these ligands may include one or more substituent groups. For ligands that include a ring structure, one or more ring carbons may be replaced with a heteroatom. Specific examples of ligands that include at least one phosphorus atom include phosphines such as tributyl phosphine [(n-Bu)$_3$P] and triphenyl phosphine (Ph$_3$P). Specific examples of ligands that include at least one phosphorus atom include phosphites such as trimethyl phosphite [(MeO)$_3$P] and triphenyl phosphite [(PhO)$_3$P]. Specific examples of ligands that include a ring nitrogen of a heterocyclic group include 1,10-phenanthroline (phen), bipyridyl (bipy) and pyridyl (Py). Specific examples of ligands that include a secondary amine include N,N'-dimethylethylenediamine (DMEDA) and N,N'-dimethyl-cyclohexanediamine (DMECA). Specific examples of ligands that include a primary amine include tetramethylenediamine (TMEDA). The ligand also may include substituted derivatives of these examples. A ligand having two or more group-V donor atoms may be present in a molar ratio with the copper of approximately 1. A ligand having only one group-V donor atom may be present in a molar ratio with the copper of approximately 1 to 2.

The reaction mixture preferably includes a solvent, which preferably is a polar, aprotic solvent. Examples of polar, aprotic solvents include DMF, DMSO, THF and $CH_2Cl_2$. Preferably the reaction mixture includes DMF as a solvent.

The reaction mixture includes the copper and the aromatic halide at an overall molar ratio of from 0.2 to 3. This overall molar ratio is the molar ratio of the total amounts of copper and of the aromatic halide in the reaction mixture over the course of the reaction, which begins with the combination of at least a portion of the copper and of the aromatic halide, and ends when the yield of the fluoroalkylarene product is no longer increasing. Preferably the reaction mixture includes the copper and the aromatic halide at an overall molar ratio of from 0.5 to 2.5. More preferably the reaction mixture includes the copper and the aromatic halide at an overall molar ratio of from 0.8 to 2, more preferably from 0.9 to 1.5, and more preferably from 0.95 to 1.1. More preferably the copper is present in a stoichiometric amount relative to the aromatic halide over the course of the reaction.

The reaction mixture preferably includes the copper and the fluoroalkyl group at an overall molar ratio of from 0.5 to 3. This overall molar ratio is the molar ratio of the total amounts of copper and of the fluoroalkyl group in the reaction mixture over the course of the reaction, which begins with the combination of at least a portion of the copper and of the fluoroalkyl group, and ends when the yield of the fluoroalkylarene product is no longer increasing. Preferably the reaction mixture includes the copper and the fluoroalkyl group at an overall molar ratio of from 0.7 to 2.5. More preferably the reaction mixture includes the copper and the fluoroalkyl group at an overall molar ratio of from 0.8 to 2, more preferably from 0.9 to 1.5, and more preferably from 0.95 to 1.1. More preferably the copper is present in a stoichiometric amount relative to the fluoroalkyl group over the course of the reaction.

The copper, the ligand and the fluoroalkyl group may form a complex in the reaction mixture. If the ligand includes one or two group-V donors, the complex may be described with an empirical formula of (L)Cu—$R_f$, where L is the ligand and $R_f$ is the fluoroalkyl group. If the ligand includes only one group-V donor, the complex may be described with an empirical formula of (L')$_2$Cu—$R_f$, where L' is the ligand and $R_f$ is the fluoroalkyl group. In each of these empirical formulas, the copper is present in a stoichiometric amount relative to the fluoroalkyl group.

In one example, a reaction mixture may be formed by combining in a solvent [Cu—O-t-Butyl]$_4$ as the copper source, 1,10-phenanthroline as the ligand, and either TMS-CF$_3$ or TMS-CF$_2$CF$_2$CF$_3$ as the fluoroalkyl group source, as shown in Scheme 1 below:

Scheme 1

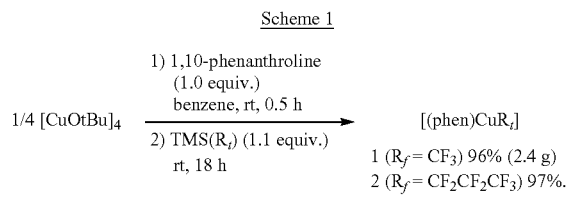

Complex 1 in Scheme 1 includes a trifluoromethyl group as the fluoroalkyl group, and complex 2 in Scheme 1 includes a perfluoropropyl group as the fluoroalkyl group.

In another example, a reaction mixture may be formed by combining a solvent with a copper-containing reagent such as [(phen)Cu—$R_f$]. The copper-containing reagent [(phen)Cu—$R_f$] may be formed as shown in Scheme 2 below:

Scheme 2

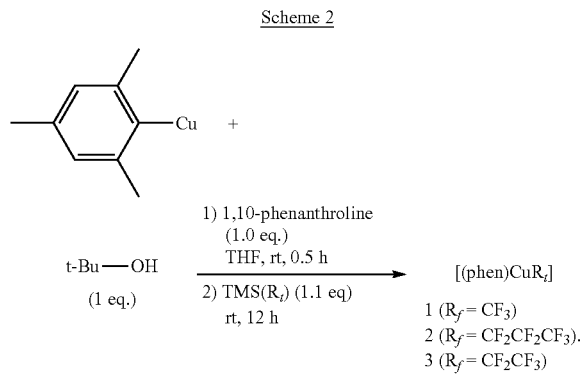

Complex 1 and complex 2 are as shown in Scheme 1. Complex 3 in Scheme 2 includes a perfluoroethyl group as the fluoroalkyl group.

When present in the reaction mixture, a portion of the copper atoms may be in the form of a complex with both the ligand and the fluoroalkyl group, and a portion of the copper atoms may be in the form of a complex with either the ligand or the fluoroalkyl group. Without being bound by any theory of operation, one possible form of such a copper complex is an ionic double salt of L$_2$Cu and Cu—(R$_f$)$_2$. In the example of complex 1 in Schemes 1 and 2, such a double salt may be denoted as [(phen)$_2$Cu][Cu(CF$_3$)$_2$]. Solution conductivity and $^{19}$F NMR measurements in DMF-d$_7$ of a combination in DMF of copper, 1,10-phenanthroline and TMS-CF$_3$ in a 1:1:1 molar ratio are described in Example 2 below. These results were consistent with the presence of both the [(phen)$_2$Cu][Cu(CF$_3$)$_2$] double salt and the (phen)Cu—CF$_3$ complex.

Thus, a substance represented in the present application as having formula (L)Cu—$R_f$ may be present in a reaction mixture as a combination of (L)Cu—$R_f$ and [(L)$_2$Cu][Cu(CF$_3$)$_2$]. Other combinations of the ligand, copper and the fluoroalkyl group also may be present in the reaction mixture. In addition, one of the components may be present in excess of a 1:1 ratio with the other components.

The fluoroalkylarene formed in the reaction mixture includes the aromatic group of the aromatic halide, and the fluoroalkyl group bonded to the aromatic group. Preferably the fluoroalkylarene is formed in a yield of at least 50%. More preferably the fluoroalkylarene is formed in a yield of at least 60%, more preferably of at least 70%, more preferably of at least 80%, and more preferably of at least 90%. Preferably these yields can be obtained by maintaining the reaction mixture at a temperature of from 25° C. to 80° C. for a period of from 6 to 30 hours. More preferably these yields can be obtained by maintaining the reaction mixture at a temperature of from 25° C. to 50° C. for a period of from 12 to 24 hours. More preferably these yields can be obtained by maintaining the reaction mixture at a temperature of from approximately 25° C. for a period of approximately 18 hours.

FIG. 1 depicts chemical structures, reaction schemes and product yields for examples of fluoroalkylation reactions of aromatic iodides. Reagent 1 included an approximately 1:1:1 molar ratio of copper, 1,10-phenanthroline ligand and trifluoromethyl group. Reagent 1 was the limiting reactant, and the reaction mixture had an overall molar ratio of copper to aromatic iodide of 0.2. The reaction of reagent 1 with a range of electron-neutral, electron-rich and electron-deficient aromatic iodides 3 gave trifluoromethylarenes 4 in good yields, which is reported in FIG. 1 as a percentage of the theoretical yield based on the equivalents of reagent 1. Yields were determined by $^{19}$F NMR analysis using 4-CF$_3$OC$_6$H$_4$OMe as internal standard, and reported as an average of two runs. For the yield identified with the superscript b, the result was obtained with reagent 1 that had been stored for over one month. The reactions occurred with aromatic iodides 3a-3p that contained a wide range of functional groups including amino, alkoxy, hydroxyalkyl, halo, keto, formyl, cyano and nitro groups. The letter designations for the aromatic iodides 3 correlate with the letter designations of the corresponding trifluoromethylarenes 4.

The synthetic results depicted in FIG. 1 were unexpected and surprising in view of conventional fluoroalkylation methods. In an example of unexpected and surprising results, the reactions of reagent 1 with aryl iodides containing alcohol, ketone or aldehyde functionalities (3f, 3g and 3h) provided the corresponding trifluoromethyl arenes in yields of 75%, 87% and 92%, respectively. In contrast, substrates containing alcohol, ketone or aldehyde functional groups typically do not tolerate the different palladium-catalyzed trifluoromethylation protocols. Moreover, the stability of the carbonyl groups on 3g and 3h toward reagent 1 contrasts with the reaction of these functional groups with CF$_3$ anions generated from the conventional treatment of Ruppert's reagent in the presence of fluoride activators.

In another example of unexpected and surprising results, bromoarene 3e and chloroarene 3m reacted selectively at the iodide. In yet another example of unexpected and surprising results, reaction of reagent 1 even occurred with 2,6-disubstituted aryl iodides 3n and 3o in good yield. The reactions of reagent 1 were more than ten times faster than the trifluoromethylation reactions reported using [(SIMes)$_2$Cu][Cu(CF$_3$)$_2$].

Figure 2:
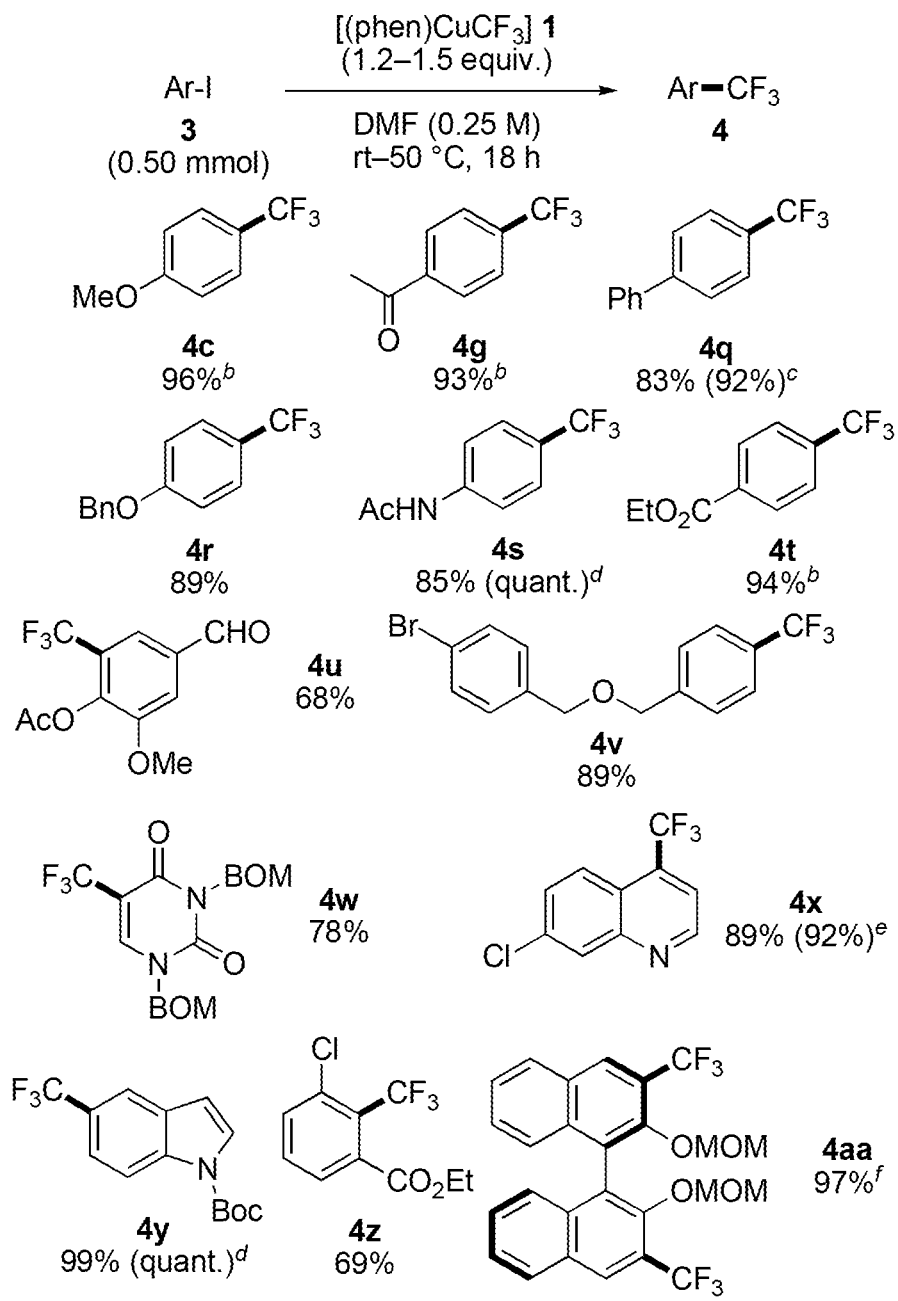
FIG. 2 depicts chemical structures, reaction schemes and product yields for examples of fluoroalkylation reactions of aromatic iodides, where the aromatic iodide was used as the limiting reactant.

FIG. 2 depicts chemical structures, reaction schemes and product yields for examples of fluoroalkylation reactions of aromatic iodides, where the aromatic iodide was used as the limiting reactant. In synthetic applications involving a multi-step sequence including the fluoroalkylation, the aromatic iodide would likely be one of the more valuable components. Thus, conditions similar to those of FIG. 2 may be used in the practical applications of this method. The reactions depicted in FIG. 2 were performed using 1.5 equiv of reagent 1 at 50° C. unless otherwise noted. For the reactions identified with the superscript b, the yield was determined by $^{19}$F NMR analysis using 4-CF$_3$OC$_6$H$_4$OMe as internal standard. For the reactions identified with the superscript c, the reaction was performed with reagent 1 that was weighed in air. For the reactions identified with the superscript d, the reaction was performed at room temperature. For the reactions identified with the superscript e, 1.2 equivalents of reagent 1 were used at room temperature. For the reactions identified with the superscript f, 3.0 equivalents of reagent 1 were used. The letter designations for the aromatic iodides 3 correlate with the letter designations of the corresponding trifluoromethylarenes 4.

Referring to FIG. 2, simple and functionalized aromatic iodides again reacted in good yield under these conditions. Reactions of aryl iodides 3c and 3g occurred in similar yield to those with the copper complex as limiting reagent. Simple aryl iodides like 3q and 3r; functionalized aryl iodides containing amide (3s), ester (3t and 3u), aldehyde (3u) and bromide (3v) functionality; and heteroaryl iodides (3w, 3x, 3y) reacted with reagent 1 to give trifluoromethylarenes 4 in good isolated yields. The functionalized aryl iodide 3z, available via metalation with Knochel's LiCl-(TMP)MgX reagent, also gave product 4z in good yield. Several heteroaromatic iodides also reacted, including quinoline 3x containing an exposed basic nitrogen. Trifluoromethylation of the 3,3'-diiodo-BINOL derivative 3aa gave the MOM-protected 3,3'-(CF$_3$)$_2$-BINOL 4aa under mild conditions. Surprisingly, it was not necessary to use a glovebox to conduct these reactions. For example, the reaction of p-phenyl iodoarene 3q with reagent 1 that was weighed quickly in air formed the trifluoromethylarene product in 92% yield.

Figure 3:
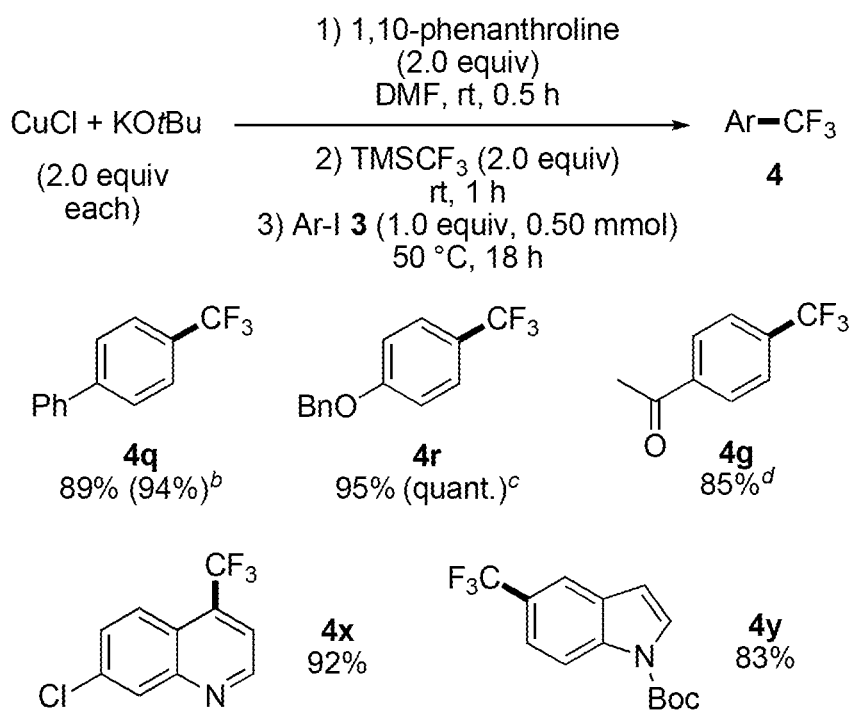
FIG. 3 depicts chemical structures, reaction schemes and product yields for examples of fluoroalkylation reactions of aromatic iodides, where the copper, ligand and fluoroalkyl source were added to the reaction mixture as separate ingredients, rather than as a 1-component reagent.

FIG. 3 depicts chemical structures, reaction schemes and product yields for examples of fluoroalkylation reactions of aromatic iodides, where the copper, fluoroalkyl source and ligand were added to the reaction mixture as separate ingredients, rather than as a 1-component reagent. Thus, a copper complex was formed in situ. Copper chloride, potassium tert-butoxide and 1,10-phenanthroline were weighed outside the glove box and then combined in DMF. The mixture was stirred under a nitrogen atmosphere for 0.5 h, and then Ruppert's reagent was added to the mixture, providing a molar ratio of copper to fluoroalkyl group (CF$_3$) to ligand of 1:1:1. Subsequent addition of aromatic iodides 3 to the mixture provided trifluoromethylarenes 4 in 83 to 99% yield. The letter designations for the aromatic iodides 3 correlate with the letter designations of the corresponding trifluoromethylarenes 4.

The reactions depicted in FIG. 3 were performed at 0.50 mmol scale without the aid of glove box during the preparation of the reaction mixture unless otherwise noted. For the reaction identified with the superscript b, the result was obtained in a glove box using a molar ratio of copper to aromatic iodide of 1.5. For the reaction identified with the superscript c, the result was obtained at 10 mmol scale for 24 hours. For the reactions identified with the superscript d, the yield was determined by $^{19}$F NMR analysis using 4-CF$_3$OC$_6$H$_4$OMe as internal standard.

Referring to FIG. 3, a selection of fluoroalkylation reactions were conducted where the copper, fluoroalkyl source and ligand were added to the reaction mixture as separate ingredients, forming a copper complex in situ. The reactions were performed with aromatic halides containing electron-donating groups, electron-withdrawing groups, potentially reactive functional groups and both electron-rich and electron-poor heterocyclic compounds. The trifluoromethylarenes 4 were produced in yields that were comparable to those observed when the same iodoarenes were reacted with reagent 1.

The addition of the copper, fluoroalkyl group source, and ligand as separate ingredients may provide advantages when performing the fluoroalkylation reactions on a larger scale. The ability to scale-up the fluoroalkylation reaction was demonstrated by the reaction of benzyloxy-substituted 3r on a 10 mmol scale, which provided 2.5 g of the trifluoromethylarene 4r after 24 h, which was a 95% yield.

Figure 4:
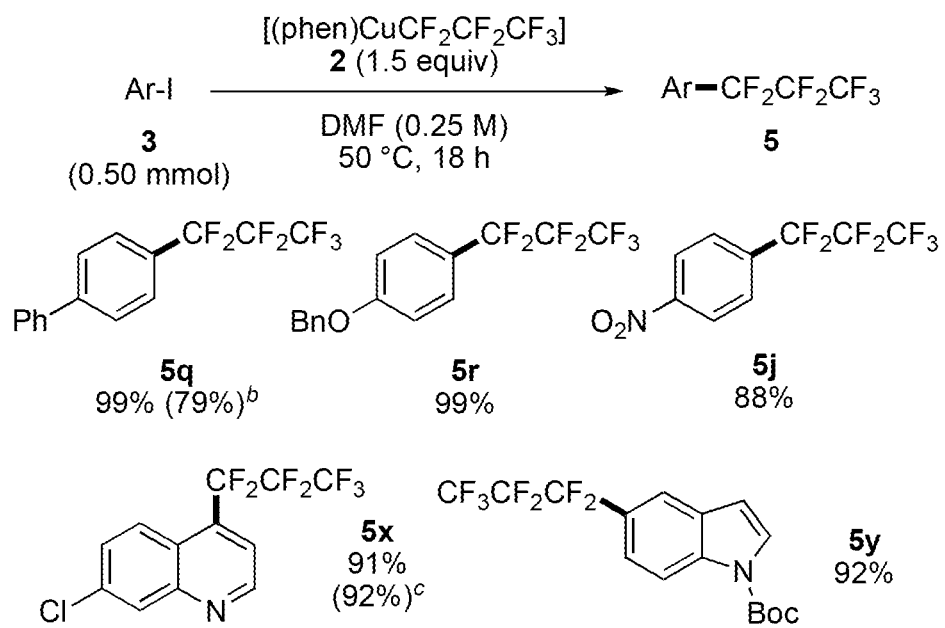
FIG. 4 depicts chemical structures, reaction schemes and product yields for examples of fluoroalkylation reactions of aromatic iodides, where the fluoroalkyl group was a perfluoropropyl group.

FIG. 4 depicts chemical structures, reaction schemes and product yields for examples of fluoroalkylation reactions of aromatic iodides, where the fluoroalkyl group was a perfluoropropyl group. The reactions depicted in FIG. 4 were performed using 1.5 equiv of reagent 2 at 50° C. unless otherwise noted. Similar to the trifluoromethylation reactions of FIGS. 1-3, perfluoropropylarenes 5 were surprisingly and unexpectedly obtained in good yield under mild reaction conditions, for aromatic iodides 3, including electron-rich and electron-poor aromatic iodides and aromatic iodides with potentially reactive quinoline and nitroarene functionality. The letter designations for the aromatic iodides 3 correlate with the letter designations of the corresponding perfluoropropylarenes 5.

Referring to FIG. 4, the yield of nitro-substituted 5i (88%) from the reaction of reagent 2 was higher than that reported from CuI+KF+TMSCF$_2$CF$_2$CF$_3$ (41%; Urata, H.; Fuchikami, T. *Tetrahedron Lett.* 1991, 32, 91.). The yield of perfluoropropylarene 5q was 99% when reagent 2 was added as a 1-component reagent. In comparison, the yield of 5q was 81% when the copper, perfluoropropyl source and ligand were added as separate ingredients and the mixture was maintained at 80° C. for 18 h. The same reaction conducted without a glove box gave the product 5q in 79% yield (reaction identified with the superscript b). For the reaction identified with the superscript c, the reaction was performed at room temperature.

Figure 5:
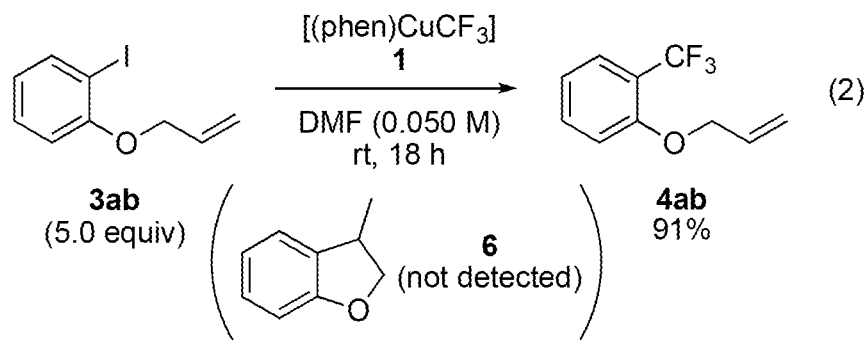
FIG. 5 depicts chemical structures, a reaction scheme and a product yield for a mechanistic study of a fluoroalkylation reaction.

FIG. 5 depicts chemical structures, a reaction scheme and a product yield for a mechanistic study of a fluoroalkylation reaction. Without being limited by any theory of operation, this study indicated that the trifluoromethylation of 2-(allyloxy)iodobenzene 3ab does not involve the formation of an aryl radical intermediate. If the trifluoromethylation of 2-(allyloxy)iodobenzene 3ab occurred through an aryl radical, one would expect to observe cyclized product 6. This product was not detected by GC-MS, however, and the reaction instead produced the trifluoromethylarene 4ab in a 91% yield.

Figure 6:
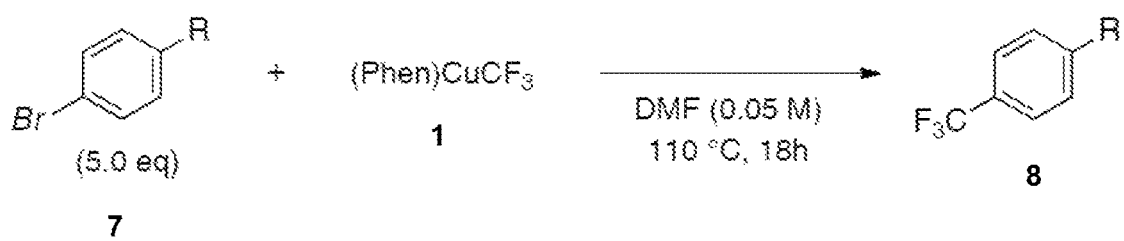
FIG. 6 depicts chemical structures, reaction schemes and product yields for examples of fluoroalkylation reactions of aromatic bromides.

FIG. 6 depicts chemical structures, reaction schemes and product yields for examples of fluoroalkylation reactions of aromatic bromides. Similar to the trifluoromethylation reactions of FIGS. 1-3, trifluoromethylarenes 8 were surprisingly and unexpectedly obtained in good yield for electron-rich, electron-poor and neutral aromatic bromides 7, including aromatic bromides with potentially reactive nitroarene functionality (7j). While the reaction temperature (110° C.) was higher than for the corresponding reactions with aromatic iodides, the reaction conditions for the aromatic bromides were still relatively mild. The letter designations for the aromatic bromides 7 correlate with the letter designations of the corresponding trifluoromethylarenes 8.

A method of forming a fluorinated molecular entity may include reacting in a reaction mixture a vinyl halide, copper, a fluoroalkyl group and a ligand, and forming a fluoroalkylvinyl compound in the reaction mixture. The vinyl halide includes an organic group that contains a vinyl group, and a halogen substituent bonded to a carbon of the vinyl group. The ligand includes at least one group-V donor. The overall molar ratio of copper to vinyl halide in the reaction mixture is from 0.5 to 3. The fluoroalkylvinyl compound formed in the reaction mixture includes the organic group that contains a vinyl group, and the fluoroalkyl group bonded to a carbon of the vinyl group.

The copper, fluoroalkyl group, ligand and reaction conditions may be as described above for fluoroalkylation of aromatic halides. An example of a fluoroalkylation reaction performed with a vinyl halide is provided in Example 12, below.

A composition, which may be useful as a reagent for the above fluoroalkylation method, consists essentially of copper, a fluoroalkyl group, and a ligand having at least one group-V donor. The molar ratio of copper to the fluoroalkyl group is approximately 1. Preferably the composition is substantially free of solvent.

The fluoroalkyl group preferably has the formula —$C_xH_{(2x-y)}F_y$, where x is from 1 to 12 and y is from 1 to (2x+1). Preferred fluoroalkyl groups include —$CF_3$, —$CF_2CF_3$, —$CH_2CF_3$, —$CH_2CH_2F$, —$CF_2CF_2CF_3$, —$CH_2CF_2CF_3$, —$CH_2CH_2CF_3$, —$CH_2CH_2CH_2F$, —$CH(CF_3)_2$ and —$CF(CF_3)_2$.

The ligand may include at least one group-V donor. Preferably the ligand includes at least one group-V atom such as phosphorus or nitrogen. More preferably the ligand includes at least one group-V atom selected from the group consisting of phosphorus, a ring nitrogen of a heterocyclic group, and an amine. Examples of ligands that include at least one phosphorus atom, a ring nitrogen of a heterocyclic group or an amine include a phenanthroline, an N,N'-disubstituted diamine, a bipyridyl, a pyridyl, a phosphine, and a phosphite. Each of these ligands may include one or more substituent groups. For ligands that include a ring structure, one or more ring carbons may be replaced with a heteroatom. Specific examples of ligands that include at least one phosphorus atom, a ring nitrogen of a heterocyclic group, or an amine include 1,10-phenanthroline (phen), tetramethylenediamine (TMEDA), N,N'-dimethylethylenediamine (DMEDA), N,N'-dimethylcyclohexanediamine (DMECA), bipyridyl (bipy), pyridyl (Py), tributyl phosphine [(n-Bu)$_3$P], triphenyl phosphine (Ph$_3$P), trimethyl phosphite [(MeO)$_3$P], triphenyl phosphite [(PhO)$_3$P] and substituted derivatives of these. A ligand having two or more group-V donor atoms may be present in a molar ratio with the copper of approximately 1. A ligand having only one group-V donor atom may be present in a molar ratio with the copper of approximately 1 to 2.

In one example, a composition consisting essentially of copper, the fluoroalkyl group, and the ligand may be prepared by combining a copper source and the ligand in a solvent to form a first mixture, and then adding a fluoroalkyl group source to form a second mixture. The composition consisting essentially of copper, the fluoroalkyl group, and the ligand may precipitate out of the solvent, and the precipitate may be isolated from the mixture, and optionally washed and/or dried, to provide a composition substantially free of solvent.

Referring to Scheme 1 above, a composition having the molecular formula of reagent 1 was isolated as an orange-red solid in 96% yield on a multigram scale from the reaction of [CuOtBu]$_4$ and 1,10-phenanthroline, followed by trimethyl(trifluoromethyl)-silane (TMS-CF$_3$, Ruppert's reagent) in one pot. Complex 1 was soluble in polar, aprotic solvents such as DMF and DMSO, partially soluble in THF and CH$_2$Cl$_2$, and insoluble in less polar solvents such as benzene and Et$_2$O. The isolated complex 1 was stable at room temperature under nitrogen atmosphere for over 1 month without decomposition.

Referring to Scheme 1 above, a composition having the molecular formula of reagent 2 was synthesized in 97% yield by an analogous reaction starting with commercially available (perfluoropropyl)-trimethylsilane instead of Ruppert's reagent.

In another example, a composition consisting essentially of copper, the fluoroalkyl group, and the ligand may be prepared by combining a copper source that includes a copper-carbon bond or a copper-nitrogen bond, an alcohol, a compound including at least one group-V donor, and a tri-organo(fluoroalkylsilane). These ingredients may be combined in any order, and may be combined in a single step or in two or more steps. Preferably the copper source, the alcohol and the compound including at least one group-V donor are combined in a first mixture having a solvent, and the tri-organo(fluoroalkylsilane) is added to the first mixture to form a second mixture. A copper-containing reagent having the general structure [(L)Cu—R$_f$] may precipitate out of the reaction mixture, and the precipitate may be isolated from the mixture, and optionally washed and/or dried, to provide a composition substantially free of solvent.

Examples of copper sources containing a copper-carbon bond include copper mesityl, Cu—C$_6$H$_5$, Cu-o-tolyl, Cu-2,6-xylyl, a Cu-enolate, a copper acetylide and a copper vinyl compound. Examples of copper sources containing a copper-nitrogen bond include Cu—N(SiCH$_3$)$_2$, Cu—N(C$_6$H$_5$)$_2$ and Cu—N(CH$_3$)$_2$. Examples of alcohols include methanol, ethanol, isopropanol, n-butyl alcohol and t-butyl alcohol. Examples of ligands and of tri-organo(fluoroalkylsilanes) are listed above.

For a compound having two or more group-V donor atoms, the compound may be present in the first mixture in a molar ratio with the copper of 0.75 to 1.5, and preferably is present in the first mixture in a molar ratio with the copper of approximately 1. For a compound having only one group-V donor atom, the compound may be present in a molar ratio with the copper of 0.75 to 2.5, and preferably is present in the first mixture in a molar ratio with the copper of approximately 1 to 2. The tri-organo(fluoroalkylsilane) may be present in the first mixture in a molar ratio with the copper of 0.75 to 1.5, and preferably is present in the first mixture in a molar ratio with the copper of approximately 1.

Referring to Scheme 2 above, a composition having the molecular formula of reagent 1 was isolated as an orange-red solid on a multigram scale from the reaction of copper mesityl, t-butyl alcohol and 1,10-phenanthroline, followed by TMS-CF$_3$ in one pot. A composition having the molecular formula of reagent 2 was prepared by an analogous reaction starting with commercially available trimethyl(perfluoropropylsilane) instead of TMS-CF$_3$. A composition having the molecular formula of reagent 3 was prepared by an analogous reaction starting with commercially available trimethyl(perfluoroethylsilane) instead of TMS-CF$_3$.

One advantage of this method of preparing a copper-containing reagent using a copper source containing a copper-carbon bond or a copper-nitrogen bond, relative to the method of Scheme 1, is that the reagent can be prepared on a scale of 20 or more grams per reaction. Another advantage of using this method of preparing a copper-containing reagent is that copper mesityl is simpler to prepare, isolate and store than is [CuOtBu].

Another composition, which may be useful as a reagent for the fluoroalkylation method, consists essentially of copper, a fluoroalkyl group, a first ligand having at least one group-V donor, and a second ligand different from the first ligand. The molar ratio of copper to the fluoroalkyl group is approximately 1. Preferably the composition is substantially free of solvent. The fluoroalkyl group and the first ligand may be as described above.

The second ligand may stabilize the composition from thermal and/or oxidative degradation, and may be released from the copper when the composition is added to a reaction mixture. The second ligand may include at least one group-V or group-VI atom, which may be a donor atom. Preferably the ligand includes at least one group-V donor atom such as phosphorus or nitrogen and/or at least one group-VI donor atom such as oxygen. More preferably the ligand includes phosphorus, a ring nitrogen of a heterocyclic group, an amine, oxygen or sulfur.

Examples of ligands that include at least one phosphorus atom, a ring nitrogen of a heterocyclic group, an amine, an oxygen atom or a sulfur atom include a phenanthroline, an N,N'-disubstituted diamine, a bipyridine, a pyridine, a trialkylamine, an azole, a phosphine, a phosphite, an ether, an amide and a sulfide. Each of these ligands may include one or more substituent groups. For ligands that include a ring structure, ore or more ring carbons may be replaced with a heteroatom. Specific examples of ligands that include at least one phosphorus atom, a ring nitrogen of a heterocyclic group, an amine, an oxygen atom or a sulfur atom include 1,10-phenanthroline, TMEDA, DMEDA, DMECA, bipy, Py, N-methylimidazole, oxazole, N-methyl pyrazole, triethylamine, (n-Bu)$_3$P, Ph$_3$P, (MeO)$_3$P, (PhO)$_3$P, diethyl ether, THF, DMF, urea, dimethyl sulfide, thiourea, acetate (OAc), and pivalate.

The fluoroalkylation methods and reagents can provide fluoroalkyl arenes with an unprecedented range of aryl iodides at temperatures from room temperature to 50° C. In comparison to conventional methods for fluoroalkylation of aromatic halides, this system can react under much milder conditions, can tolerate a wider range of functional groups, can tolerate basic heterocycles, reacts with more hindered substrates, and can be extended to perfluoroalkylation. The method also may be carried out with a total cost that is much less than the conventional palladium-catalyzed systems involving CF$_3$ nucleophiles or electrophiles. The reagent may be prepared from easily available, inexpensive reagents in one pot and can be used in situ or as an isolated composition.

The following examples are provided to illustrate one or more preferred embodiments of the invention. Numerous variations can be made to the following examples that lie within the scope of the invention.

EXAMPLES

General Procedures.

All manipulations were conducted under an inert atmosphere using a nitrogen-filled glovebox (Innovative Technologies, Newburyport, Mass.) equipped with an oxygen sensor (working oxygen level <20.0 ppm) and low-temperature refrigeration unit (−30° C.), unless otherwise noted. All reactions were conducted in oven-dried 4-mL or 20-mL vials fitted with a Teflon-lined screw cap under an atmosphere of nitrogen, unless otherwise noted.

All reactions were run with anhydrous solvents. The solvents Et$_2$O, THF, benzene, and toluene were degassed with argon and passed through a column of activated alumina in a solvent purification system from Innovative Technologies. Anhydrous DMF was purchased from Aldrich (St. Louis, Mo.) and used as received.

Materials.

Copper(I) chloride (99.999%) was purchased from STREM CHEMICALS, INC. (Newburyport, Mass.). Copper(I) chloride (≥99%), lithium tert-butoxide (97%), potassium tert-butoxide (95% or ≥97%), anhydrous t-butyl alcohol, 1,10-phenanthroline (phen), 2,2'-bipyridyl (bipy), 4,4'-di-tert-butyl-2,2'-bipyridine (dtbpy), (perfluoropropyl)trimethylsilane (TMSCF$_2$CF$_2$CF$_3$) and 4-(trifluoromethoxy)anisole (internal standard of $^{19}$F NMR analysis) were purchased from Aldrich. Trimethyl(trifluoromethyl)silane (Ruppert's reagent, TMSCF$_3$) was purchased from Matrix Scientific. Iodobenzene (3a), 4-iodoanisole (3c), 4-bromoiodobenzene (3e), 4-iodobenzyl alcohol (3f), 4-iodoacetophenone (3g), 4-iodobenzaldehyde (3h), 4-iodobenzonitrile (3i), 4-nitroiodobenzene (3j), 2-iodotoluene (3k), 2-iodoanisole (3l), 2-iodo-1,3-dimethylbenzene (3n), 1-iodo-2,6-dimethoxybenzene (3o), 4-iodobiphenyl (3q), 4-(benzyloxy)iodobenzene (3r), ethyl 4-iodobenzoate (3t), 7-chloro-4-iodoquinoline (3x) were purchased from Aldrich. 4-Butyliodobenzene (3b) and 3-iodopyridine (3p) were purchased from Alfa Aesar. 2-Chloroiodobenzene (3m) was purchased from Lancaster. All the commercially available reagents were used as received. [CuOtBu]$_4$ was prepared from CuCl (Strem) and LiOtBu according to literature procedures (Tsuda, T.; Hashimoto, T.; Saegusa, T. *J. Am. Chem. Soc.* 1972, 94, 658; Lemmen, T. H.; Goeden, G. V.; Huffman, J. C.; Geerts, R. L.; Caulton, K. G. *Inorg. Chem.* 1990, 29, 3680.)

The following were prepared according to the literature procedures: 4-Iodo-N,N-dimethylaniline (3d; Monnereau, C.; Blart, E.; Odobel, F. *Tetrahedron Lett.* 2005, 46, 5421.), N-(4-iodophenyl)acetamide (3s; Björnestedt, R.; Zhong, G.; Lerner, R. A.; Barbas III, C. F. *J. Am. Chem. Soc.* 1996, 118, 11720.), 4-formyl-2-iodo-6-methoxyphenyl acetate (3u; Liao, Y.; Fathi, R.; Yang, Z. WO2004000764.), 1,3-bis(benzyloxymethyl)-5-iodopyrimidine-2,4(1H,3H)-dione (3w; DeFrees, S. A.; Reddy, K. S.; Cassady, J. M. *Synth. Commun.* 1988, 18, 213.), N-tert-butoxycarbonyl-5-iodoindole (3y; Furuya, T.; Storm, A. E.; Ritter, T. *J. Am. Chem. Soc.* 2009, 131, 1662.), ethyl 3-chloro-2-iodobenzoate (3z; Lin, W.; Baron, O.; Knochel, P. *Org. Lett.* 2006, 8, 5673.), (R)-3,3'-diiodo-2,2'-bis(methoxymethoxy)-1,1'-binaphthyl (3aa; Wu, T. R.; Shen, L.; Chong, J. M. *Org. Lett.* 2004, 6, 2701; Milburn, R. R.; Hussain, S. M. S.; Prien, O.; Ahmed, Z.; Snieckus, V. *Org. Lett.* 2007, 9, 4403.), and 1-(allyloxy)-2-iodobenzene (3ab; Molander, G. A.; Harring, L. S. *J. Org. Chem.* 1990, 5.5, 6171.).

1-Bromo-4-[(4-iodobenzyloxy)methyl]benzene (3v) was prepared using an non-optimized procedure as follows. To a stirred solution of 4-iodobenzyl alcohol (1.33 g, 5.5 mmol, 1.1 equiv) in DMF (40 mL) at 0° C. was added NaH (240 mg, 60% in mineral oil, 6.0 mmol, 1.2 equiv), and the mixture was warmed to room temperature and stirred for 30 min. The mixture was cooled to 0° C., and 4-bromobenzyl bromide (1.25 g, 5.0 mmol, 1.0 equiv) and tetra-n-butylammonium iodide (92.3 mg, 0.25 mmol, 0.050 equiv) were added. The reaction mixture was warmed to room temperature, stirred for 2 h and quenched with saturated aqueous NH₄Cl solution. The mixture was extracted with Et₂O, and the organic layer was washed with 1 M aqueous HCl solution and brine and dried over Na₂SO₄. After evaporation of the solvent, the crude mixture was purified by flash silica gel column chromatography (hexane/Et₂O=400/1 to 20/1) to give 1-bromo-4-[(4-iodobenzyloxy)methyl]benzene (3v) as a white solid (1.02 g, 51% yield). $^1$H NMR (400 MHz, CDCl₃): δ 7.68 (d, J=8.4 Hz, 2 H), 7.48 (d, J=8.4 Hz, 2 H), 7.22 (d, J=8.4 Hz, 2 H), 7.10 (d, J=8.4 Hz, 2 H), 4.49 (s, 4 H). $^{13}$C{$^1$H} NMR (125 MHz, CDCl₃): δ 137.9, 137.8, 137.2, 131.8, 129.8, 129.6, 121.9, 93.4, 71.8, 71.7. Anal. calcd. for C₁₄H₁₂BrIO: C, 41.72; H, 3.00; found: C, 41.71; H, 2.77.

Instrumentation.

Organic solutions were concentrated by rotary evaporation at 25-40° C. Flash silica gel column chromatography was conducted with Silicycle Silica-P Flash Silica Gel, eluting with pentane or a mixture of pentane and Et₂O. TLC was conducted with EMD Silica Gel 60 F₂₅₄ (250 micrometer layer thickness). The products were visualized by UV light and staining with ceric ammonium molybdate (CAM).

NMR spectra were acquired on 400 MHz and 500 MHz Varian Unity or Innova instruments at the University of Illinois VOICE NMR facility. NMR spectra were processed with MestReNova 5.0 (Mestrelab Research SL). Chemical shifts are reported in ppm and referenced to residual solvent peaks (CHCl₃ in CDCl₂: 7.26 ppm for $^1$H and 77.0 ppm for $^{13}$C; DMF-d₆ in DMF-d₇: 2.91 ppm for $^3$H and 162.7 ppm for $^{13}$C) or to an external standard (1% CFCl₃ in CDCl₃: 0 ppm for $^{19}$F). Coupling constants are reported in hertz. Benzene-d₆ and DMF-d₇ were dried over activated MS 4 A prior to use. THF-d₈ and dichloromethane-d₉ were purchased from Aldrich and used as received.

All GC-MS analyses were conducted with an Agilent 6890N GC equipped with an HP-5 column (25 m×0.20 mm ID×0.33 micrometer film) and an Agilent 5973 Mass Selective Detector. The temperature for each run was held at 50° C. for 2 min, ramped from 50° C. to 300° C. at 5° C./min, and held at 300° C. for 5 min.

Elemental analyses were performed by the University of Illinois at Urbana-Champaign Microanalysis Laboratory and by Robertson Microlit Laboratories, Inc. (Madison, N.J.). Optical rotations were measured on a Rudolph Instruments (Denville, N.J.) Autopol IV polarimeter.

Example 1

Formation of
(1,10-Phenanthroline)(trifluoromethyl)copper(I) (1)

To an oven-dried 250-mL round-bottomed flask equipped with a stir bar were added [CuOtBu]₄ (1.094 g, 2.00 mmol, 8.00 mmol for monomeric CuOtBu), 1,10-phenanthroline (1.442 g, 8.00 mmol, 1.00 equiv) and benzene (80 ml). The flask was sealed with a septum and the dark purple mixture was stirred at room temperature for 30 min, then TMSCF₃ (1.31 mL, 8.80 mmol, 1.1 equiv) was added dropwise. The mixture was stirred at room temperature for 18 h to give a red-orange suspension. The suspension was filtered through a medium fritted funnel, and the solid was washed with Et₂O (50 ml) and dried under vacuum to give (1,10-phenanthroline)-(trifluoromethyl)copper(I) (1) as an orange solid (2.397 g, 96% yield).

$^1$H NMR (400 MHz, DMF-d₇) δ 9.18 (d, J=4.2 Hz, 2 H), 8.89 (d, J=8.0 Hz, 2 H), 8.31 (s, 2 H), 8.10 (dd, J=4.2, 8.0 Hz, 2 H). $^{13}$C{$^1$H} NMR (100 MHz, DMF-d₇) δ 150.4, 144.2, 138.3, 130.0, 127.8, 126.5 (note that a carbon peak for CF₃ was not observed due to (1) dynamic behavior of the complex (see below), (2) broadening the peak through Cu—C coupling and (3) splitting of the peak through C—F coupling). $^{19}$F NMR (376 MHz, DMF-d₇): -22.6 (br), -30.9 (s). Anal. Calcd for C₁₃H₈CuN₂F₃: C, 49.92; H, 2.58; N, 8.96; F, 18.22; Found: C, 49.74; H, 2.52; N, 8.99; F, 18.17.

Example 2

Characterization of (phen)Cu—CF₃ (1)

Conductivity Measurements: To a 5-mL volumetric flask was added (1,10-phenanthroline)(trifluoromethyl)copper(I) (1) (15.6 mg, 0.050 mmol), and DMF was added to the flask to the 5 mL mark to give a 0.010 M solution of 1 in DMF. A portion of the 0.010 M solution (0.50 mL, 0.0050 mmol) was transferred to another 5-mL volumetric flask and diluted with DMF to the 5 mL mark to give a 1.0 mM solution of 1. The conductivity of the 1.0 mM solution of 1 was 26 $Ω^{-1}cm^2mol^{-1}$. The same procedure was followed for the reference samples ferrocene (neutral) and tetra-n-butylammonium tetraphenylborate (ionic), and the conductivity for these samples was 0.5 and 50.5 $Ω^{-1}cm^2mol^{-1}$, respectively.

$^{19}$F NMR Peak Ratio in Different Solvents: (1,10-Phenanthroline) (trifluoromethyl)copper(I) (1) (2.2 mg, 0.0070 mmol) was dissolved in either dichloromethane-d₂, THF-d₈, or DMF-d₇ (0.70 mL, 0.010 M for 1), and the ratio of the two peaks at -22.6 and -30.9 ppm was measured by $^{19}$F NMR analysis. The observed ratio was 76/24 in dichloromethane-d₂, 68/32 in THF-d₈, and 21/79 in DMF-d₇.

Dynamic Behavior in Solution: The $^{19}$F NMR spectrum of 1 in DMF-d₇ consisted of two peaks at -22.6 and -30.9 ppm. Based on the peak ratio observed in the solvents with different polarity, we proposed that the peak at -30.9 ppm corresponded to species with the ionic "double salt" structure ([(phen)₂Cu][Cu(CF₃)₂]) and the peak at -22.6 ppm to a species with the neutral structure (phen)CuCF₃. The presence of ionic species in solution was verified by the conductivity measurement of 1 in DMF described above. This structural assignment agrees with the previous reports by Burton (Wiemers, D. M.; Burton, D. J. *J. Am. Chem. Soc.* 1986, 108, 832.) and Vicic (Dubinina, G. G.; Ogikubo, J.; Vicic, D. A. *Organometallics* 2008, 27, 6233.) in which two $^{19}$F NMR resonances were reported for the N-heterocyclic carbene-ligated copper trifluoromethyl complex. The dynamic behavior of 1 in solution was also evidenced by the different peak ratio in the solvents with different polarity.

Example 3

Formation of
(1,10-Phenanthroline)(perfluoropropyl)copper(I) (2)

To a 40-mL vial equipped with a stir bar were added [CuOtBu]4 (274 mg, 0.50 mmol, 2.00 mmol for monomeric CuOtBu, 1.0 equiv), 1,10-phenanthroline (360 mg, 2.00 mmol, 1.00 equiv) and benzene (20 mL). The dark purple mixture was stirred at room temperature for 30 min, at which time TMSCF₂CF₂CF₃ (446 µL, 1.1 mmol, 1.1 equiv) was added dropwise. The mixture was stirred at room temperature for 18 h to give a dark purple suspension. The suspension was filtered through a medium fritted funnel, and the solid was washed with Et₂O (10 mL) and dried under vacuum to give (1,10-phenanthroline)(perfluoropropyl)copper(I) (2) as a brown solid (801 mg, 97% yield). The same reaction was also performed on 3.0 mmol scale using 411 mg of [CuOtBu]$_4$, 669 mg of 1,10-phenanthroline and 669 μL of TMSCF$_2$CF$_2$CF$_3$ in 30 mL of benzene to give 2 (1149 mg, 93% yield).

$^1$H NMR (400 MHz, DMF-d$_7$) δ 9.16 (s, 2 H), 8.87 (brs, 2H), 8.26 (brs, 2H), 8.12-8.09 (m, 2H). $^{13}$C NMR (125 MHz, DMF-d$_7$) δ 162.9, 162.7, 162.5, 150.6, 144.3, 144.3, 138.4, 130.0, 127.8, 126.5 (note that a carbon peak for CF$_3$ was not observed due to (1) dynamic behavior of the complex (see below), (2) broadening the peak through Cu—C coupling and (3) splitting of the peak through C—F coupling). $^{19}$F NMR (375 MHz, DMF-d$_7$) δ −79.6, −80.3 (t, J$_{C-F}$=8.9 Hz) −109.6, −117.4, −125.2, −127.2. Anal. Calcd for C$_{15}$H$_8$CuN$_2$F$_7$: C, 43.65; H, 1.95; N, 6.79; Found: C, 43.56; H, 2.03; N, 6.95. Conductivity (1 mM in DMF): 13.2 Ω$^{-1}$cm$^2$mol$^{-1}$.

Example 4

Fluoroalkylation Reactions of Aromatic Iodides (3) Using (phen)Cu—CF$_3$ (1) as Limiting Agent To a 4-mL vial equipped with a stir bar were added 1 (10.9 mg, 0.035 mmol), ArI 3 (if solid, 0.175 mmol, 5.0 equiv) and 4-(trifluoromethoxy)anisole (internal standard for $^{19}$F NMR analysis) in DMF (0.70 mL, 0.050 M, 0.035 mmol). To the mixture was added ArI 3 (if liquid, 0.175 mmol, 5.0 equiv), and the mixture was stirred at room temperature. After 18 h, the stirring was stopped, and the reaction mixture was transferred to an NMR tube, and the yield of the product was measured by $^{19}$F NMR analysis with the following parameters after reduction of the sw (sweep width) to include both standard (−58.6 ppm) and product peaks: at=10 (s), d1=10 (s), pw90=15.5 (μs), pw=15.5 (μs) and nt=4. Structures and yields for products 4a-4p are shown in FIG. 1.

Example 5

Comparison of (phen)Cu—CF$_3$ (1) and [(SIMes)$_2$Cu][Cu(CF$_3$)$_2$]

[(SIMes)$_2$Cu][Cu(CF$_3$)$_2$] was prepared according to literature procedures (Dubinina, G. G.; Ogikubo, J.; Vicic, D. A. *Organometallics* 2008, 27, 6233.). To a 4-mL vial equipped with a stir bar were charged 1 (7.8 mg, 0.025 mmol) or [(SIMes)$_2$Cu][Cu(CF$_3$)$_2$](11.0 mg, 0.025 mmol) and 4-(trifluoromethoxy)anisole in either DMF or a mixture of DMI and benzene (1.5/7.5) (0.050 M, 0.50 mL, 0.025 mmol). To the mixture was added ArI 3b (22 μL, 0.13 mmol, 5.0 equiv), and the mixture was stirred at room temperature (for DMF; standard conditions for 1) or 50° C. (for DMI/benzene; standard conditions reported by Dubinina et al.). After 1 and 18 h (for DMF) or 1, 12 and 28 h (for DMI/benzene), the mixture was transferred to an NMR tube, and the yield of the product 4b was measured by $^{19}$F NMR analysis. The yields of the product 4b were: 19 (1 h) and 88 (18 h) % for the reaction of 1 in DMF; 0.7 (1 h) and 8.7 (18 h) % for the reaction of [(SIMes)$_2$Cu][Cu(CF$_3$)$_2$] in DMF; 85 (1 h), 92 (12 h) and 91 (28 h) % for the reaction of 1 in DMI/benzene; 8.3 (1 h), 53 (12 h) and 70 (28 h) % for the reaction of [(SIMes)$_2$Cu][Cu(CF$_3$)$_2$] in DMI/benzene.

Example 6

Fluoroalkylation Reactions with (phen)Cu—CF$_3$ (1) and Using Aromatic Iodide (3) as Limiting Agent To a 20-mL vial equipped with a stir bar was added ArI 3 (if solid, 0.50 mmol), 1 (235 mg, 0.75 mmol, 1.5 equiv) and DMF (2.0 ml). Then ArI 3 (if liquid, 0.50 mmol) was added, and the mixture was stirred at room temperature or 50° C. After 18 h, the stirring was stopped, and the reaction mixture was diluted with Et$_2$O and filtered through a pad of Celite. The Celite pad was washed with Et$_2$O. The combined filtrate was washed with 1M aqueous HCl, saturated aqueous NaHCO$_3$ solution and brine, and dried over Na$_2$SO$_4$. After filtration and evaporation of the solvent, the crude mixture was purified by flash silica gel column chromatography using pentane/Et$_2$O or pentane as eluent to give ArCF$_3$ 4. Structures and yields for the products are shown in FIG. 2, and experimental details are below.

4-(Trifluoromethyl)anisole (4c; Iwanaga, K.; Kobayashi, J.; Kawashima, T. *Tetrahedron* 2007, 63, 10127.): Reaction was performed on 0.50 mmol scale using 1.5 equiv of 1 at 50° C. for 18 h to give 4c (51.6 mg, 59% yield). The isolated yield of 4c was low due to volatility of the product. The same reaction was performed under the same reaction condition with 4-CF$_3$OC$_6$H$_4$OMe (0.50 mmol, 1.0 equiv) as internal standard to give 4c (92%, NMR yield). Pentane was used as eluent for column chromatography. $^1$H NMR (500 MHz, CDCl$_3$) δ: 7.56 (d, 2H, J=9.0 Hz), 6.67 (d, 2H, J=9.0 Hz), 3.85 (s, 3H). $^{13}$C{$^1$H} NMR (125 MHz, CDCl$_3$) δ: 162.0, 126.9 (q, J$_{C-F}$=3.9 Hz), 124.5 (q, J$_{C-F}$=270 Hz), 122.6 (q, J$_{C-F}$=32.5 Hz), 113.9, 55.4. $^{19}$F NMR (469 MHz, CDCl$_3$) δ: −62.0.

4′-(Trifluoromethyl)acetophenone (4g; Arisawa, M.; Suwa, K.; Yamaguchi, M. *Org. Lett.* 2009, 11, 625.): Reaction was performed on 0.50 mmol scale using 1.5 equiv of 1 at 50° C. for 18 h to give 4g (55.7 mg, 54% yield). The isolated yield of 4g was low due to volatility of the product. The same reaction was performed under the same reaction condition with 4-CF$_3$OC$_6$H$_4$OMe (0.50 mmol, 1.0 equiv) as internal standard to give 4g (93% NMR yield). Pentane was used as eluent for column chromatography. $^1$H NMR (500 MHz, CDCl$_3$) δ: 8.05 (d, 2H, J=8.0 Hz), 7.72 (d, 2H, J=8.0 Hz), 2.64, (s, 3H). $^{13}$C{$^1$H} NMR (125 MHz, CDCl$_3$) δ: 196.9, 139.6, 134.4 (q, J$_{C-F}$=32.5 Hz), 128.6, 125.6 (q, J$_{C-F}$=3.6 Hz), 123.6 (q, J$_{C-F}$=271 Hz), 26.7. $^{19}$F NMR (469 MHz, CDCl$_3$) δ: −63.6.

4-(Trifluoromethyl)biphenyl (4q; Ackermann, L.; Potukuchi, H. K.; Althammer, A.; Born, Robert; Mayer, Peter. *Org. Lett.* 2010, 12, 1004.): Reaction was performed on 0.50 mmol scale using 1.5 equiv of 1 at 50° C. for 18 h to give 4q (92.2 mg, 83% yield). The same reaction was performed using 1.2 equiv of 1 at rt for 18 h to give 4q (102.3 mg, 92% yield). Pentane was used as eluent for column chromatography. $^1$H NMR (400 MHz, CDCl$_3$) δ: 7.76-7.66 (m, 4H), 7.64-7.58 (m, 2H), 7.52-7.41 (m, 3H). $^{13}$C{$^1$H} NMR (125 MHz, CDCl$_3$) δ: 144.7, 139.7, 130.1 (q, J$_{C-F}$=32.2 Hz), 129.0, 128.2, 127.4, 127.3, 125.7 (q, J$_{C-F}$=3.8 Hz), 124.3 (q, J$_{C-F}$=271 Hz). $^{19}$F NMR (469 MHz, CDCl$_3$) δ: −62.8. Anal. Calcd for C$_{13}$H$_9$F$_3$: C, 70.27; H, 4.08; Found: C, 69.98; H, 3.98.

The reaction was also conducted outside glove box. In this case, 1 (0.75 mmol, 1.5 equiv) and 3q (0.50 mmol) were weighted into a 20-mL vial outside glove box and the vial was evacuated and refilled with dry nitrogen (twice). Then DMF (2.0 mL) was added and the reaction mixture was stirred at 50° C. for 18 h to give 4q (101.8 mg 92% yield).

1-(Benzyloxy)-4-(trifluoromethyl)benzene (4r; Pratt, D. A.; de Heer, M. I.; Mulder, P.; Ingold, K. U. *J. Am. Chem. Soc.* 2001, 123, 5518.): Reaction was performed on 0.50 mmol scale using 1.5 equiv of 1 at 50° C. for 18 h to give 4r (118.1 mg, 89% yield). Pentane was used as eluent for column chromatography. $^1$H NMR (400 MHz, CDCl$_3$) δ: 7.46-7.37 (m, 7H), 7.07 (d, 2H, J=8.8 Hz), 5.17, (s, 2H).

$^{13}C\{^1H\}$ NMR (125 MHz, CDCl$_3$) δ: 161.1, 136.2, 128.7, 128.2, 127.4, 126.9 (q, $J_{C-F}$=3.6 Hz), 124.4 (q, $J_{C-F}$=270 Hz), 123.0 (q, $J_{C-F}$=32.6 Hz), 114.8, 70.1. $^{19}F$ NMR (469 MHz, CDCl$_3$) δ: −61.9. Anal. Calcd for C$_{14}$H$_{11}$F$_3$O: C, 66.66; H, 4.40; Found: C, 66.41; H, 4.21.

N-[4-(Trifluoromethyl)phenyl]acetamide (4s; O'Connor, C. J.; McLennan, D. J.; Calvert, D. J.; Lomax, T. D.; Porter, A. J.; Rogers, D. A. *Aust. J. Chem.* 1984, 37, 497.): Reaction was performed on 0.50 mmol scale using 1.5 equiv of 1 at 50° C. for 18 h to give 4s (86.8 mg, 83% yield). The same reaction was performed using 1.5 equiv of 1 at rt for 18 h to give 4s (101.8 mg, quantitative). Pentane/ether mixture (2/1 to 0/1) was used for column chromatography. $^1H$ NMR (500 MHz, CDCl$_3$) δ: 7.64-7.55 (m, 5H), 2.21 (s, 3H). $^{13}C\{^1H\}$ NMR (125 MHz, CDCl$_3$) δ: 168.8, 140.9, 126.2 (q, $J_{C-F}$=3.6 Hz), 125.8 (q, $J_{C-F}$=31.4 Hz), 124.0 (q, $J_{C-F}$=270 Hz), 119.4, 24.6. $^{19}F$ NMR (469 MHz, CDCl$_3$) δ: −62.3.

Ethyl 4-(trifluoromethyl)benzoate (4t; Shang, R.; Fu, Y.; Li, J.-B.; Zhang, S.-L.; Guo, Q.-X.; Liu, L., *J. Am. Chem. Soc.* 2009, 131, 5738; Oishi, M.; Kondo, H.; Amii, H. *Chem. Commun.* 2009, 1909.): Reaction was performed on 0.50 mmol scale using 1.5 equiv of 1 at 50° C. for 18 h to give 4t (34.5 mg, 32% yield). The isolated yield of 4t was low due to volatility of the product. The same reaction was performed under the same reaction condition with 4-CF$_3$OC$_6$H$_6$OMe as internal standard (0.50 mmol, 1.0 equiv) to give 4t (94%, NMR yield). Pentane was used as eluent for column chromatography. $^1H$ NMR (500 MHz, CDCl$_3$) δ: 8.15 (d, 2H, J=8.0 Hz), 7.70 (d, 2H, J=8.0 Hz), 4.41 (q, 2H, J=7.0 Hz), 1.41, (t, 3H, J=7.0 Hz). $^{13}C\{^1H\}$ NMR (125 MHz, CDCl$_3$) δ: 165.4, 134.3 (q, $J_{C-F}$=32.6 Hz), 133.7, 129.9, 125.3 (q, $J_{C-F}$=3.8 Hz), 123.6 (q, $J_{C-F}$=271 Hz), 61.5, 14.2. $^{19}F$ NMR (469 MHz, CDCl$_3$) δ: −63.6.

4-Formyl-2-methoxy-6-(trifluoromethyl)phenyl acetate (4u) Reaction was performed on 0.50 mmol scale using 1.5 equiv of 1 at 50° C. for 18 h to give 4u (89.0 mg, 68% yield). Pentane/Ether=5/1 was used for column chromatography. $^1H$ NMR (500 MHz, CDCl$_3$) δ: 9.97 (s, 1H), 7.74 (s, 1H), 7.67 (s, 1H), 3.94 (s, 3H), 2.36 (s, 3H). $^{13}C\{^1H\}$ NMR (125 MHz, CDCl$_3$) δ: 189.7, 167.2, 153.1, 142.9 (q, $J_{C-F}$=1.6 Hz), 134.5, 125.2 (q, $J_{C-F}$=32.1 Hz), 122.2 (q, $J_{C-F}$=272 Hz), 121.2 (q, $J_{C-F}$=4.6 Hz), 113.9, 56.6, 20.2. $^{19}F$ NMR (469 MHz, CDCl$_3$) δ: −62.7. Anal. Calcd for C$_{11}$H$_9$F$_3$O$_4$: C, 50.39; H, 3.46; Found: C, 50.43; H, 3.29.

1-(4-Bromobenzyloxymethyl)-4-(trifluoromethyl)benzene (4v) Reaction was performed on 0.50 mmol scale using 1.5 equiv of 1 at 50° C. for 18 h to give 4v (154.4 mg, 89% yield). The same reaction was performed using 1.5 equiv of 1 at rt for 18 h to give 4v (145.0 mg, 84% yield). Pentane was used for column chromatography. $^1H$ NMR (400 MHz, CDCl$_3$) δ: 7.63 (d, 2H, J=8.0 Hz), 7.52-7.47 (m, 4H), 7.27-7.25 (m, 2H), 4.61, (s, 2H), 4.54 (s, 2H). $^{13}C\{^3H\}$ NMR (125 MHz, CDCl$_3$) δ: 142.1, 136.8, 131.6, 129.8 (q, $J_{C-F}$=32.1 Hz), 129.3, 127.6, 125.3 (q, $J_{C-F}$=3.8 Hz), 124.1 (q, $J_{C-F}$=271 Hz), 120.9, 71.7, 71.3. $^{19}F$ NMR (469 MHz, CDCl$_3$) δ: −62.9. Anal. Calcd for C$_{15}$H$_{15}$BrF$_3$O: C, 52.20; H, 3.50; Found: C, 52.47; H, 3.78.

1,3-Bis(benzyloxymethyl)-5-(trifluoromethyl)pyrimidine-2,4(1H,3H)-dione (4w; DeFrees, S. A.; Reddy, K. S.; Cassady, I. M. *Synth. Commun.* 1988, 18, 213.): Reaction was performed on 0.50 mmol scale using 1.5 equiv of 1 at 50° C. for 18 h to give 4w (162.9 mg, 78% yield). Ether and EtOAc was used for extraction. Pentane/Ether=2/1 was used for column chromatography. $^1H$ NMR (500 MHz, CDCl$_3$) δ: 7.66 (s, 1H), 7.37-7.25 (m, 10H), 5.45 (s, 2H), 5.26 (s, 2H), 4.70 (s, 2H), 4.64 (s, 2H). $^{13}C\{^1H\}$ NMR (125 MHz, CDCl$_3$) δ: 158.1, 150.5, 142.4, (q, $J_{C-F}$=11.5 Hz), 137.6, 136.2, 128.7, 128.5, 128.4, 127.9, 127.8, 127.6, 121.5 (q, $J_{C-F}$=269 Hz), 105.3 (q, $J_{C-F}$=33.1 Hz), 77.7, 72.6, 72.6, 70.6. $^{19}F$ NMR (469 MHz, CDCl$_3$) δ: −64.5. Anal. Calcd for C$_{21}$H$_{19}$F$_3$N$_2$O$_4$: C, 60.00; H, 4.56; N, 6.66; Found: C, 60.17; H, 4.49; N, 6.67.

7-Chloro-4-(trifluoromethyl)quinoline (4x): Reaction was performed on 0.50 mmol scale using 1.5 equiv of 1 at 50° C. for 18 h to give 4x (102.8 mg, 89% yield). The same reaction was performed using 1.2 equiv of 1 at rt for 18 h to give 4x (106.4 mg, 92% yield). In this substrate, different quenching method was used. After stirring 18 h, the mixture was poured into 29% aqueous ammonium hydroxide solution (20 mL) and extracted with ether (20 mL×3). Then, the organic layers were combined and dried over anhydrous NaSO$_4$ and filtrated and evaporated. The resulting crude mixture was diluted with ether and wash 1 M HCl, sat. NaHCO$_3$ and brine, then dried over Na$_2$SO$_4$. After filtration and evaporation of the solvent, the crude mixture was purified by flash silica gel column chromatography using pentane/Et$_2$O=10/1 as eluent to give ArCF$_3$ 4x. $^1H$ NMR (500 MHz, CDCl$_3$) δ: 9.02 (d, 1H, J=4.0 Hz), 8.18 (d, 1H, J=1.5 Hz), 8.03 (d, 1H, J=8.5 Hz), 7.66 (d, 1H, J=4.0 Hz), 7.60 (dd, 1H, J=8.5, 1.5 Hz). $^{13}C\{^1H\}$ NMR (125 MHz, CDCl$_3$) δ: 150.6, 149.3, 136.3, 134.3 (q, $J_{C-F}$=32.0 Hz), 129.3, 125.2 (q, $J_{C-F}$=2.1 Hz), 123.1 (q, $J_{C-F}$=273 Hz), 121.2, 119.8, 118.0 (q, $J_{C-F}$=5.3 Hz). $^{19}F$ NMR (469 MHz, CDCl$_2$) δ: −62.0. Anal. Calcd for C$_{10}$H$_5$ClF$_3$N: C, 51.86; H, 2.18; N, 6.05; Found: C, 51.82; H, 1.99; N, 5.91.

tert-Butyl 5-(trifluoromethyl)-1H-indole-1-carboxylate (4y): Reaction was performed on 0.50 mmol scale using 1.5 equiv of 1 at 50° C. for 18 h to give 4y (141.2 mg, 99% yield). The same reaction was performed using 1.5 equiv of 1 at rt for 18 h to give 4y (145.2 mg, quantitative). Pentane/ Ether=10/1 was used for column chromatography. $^1H$ NMR (400 MHz, CDCl$_3$) δ: 8.26 (d, 1H, J=8.8 Hz), 7.85 (d, 1H, J=1.2 Hz), 7.69 (d, 1H, J=3.6 Hz), 7.56 (dd, 1H, J=8.8, 1.2 Hz), 6.63 (d, 1H, J=3.6 Hz), 1.69 (s, 9H). $^{13}C\{^1H\}$ NMR (125 MHz, CDCl$_3$) δ: 149.3, 136.7, 130.1, 127.5, 124.9 (q, $J_{C-F}$=32.0 Hz), 124.8 (q, $J_{C-F}$=270 Hz), 120.9 (q, $J_{C-F}$=3.3 Hz), 118.3 (q, $J_{C-F}$=4.0 Hz), 115.4, 107.3, 84.4, 28.1. $^{19}F$ NMR (376 MHz, CDCl$_3$) δ: −61.5. Anal. Calcd for C$_{14}$H$_{14}$F$_3$NO$_2$: C, 58.95; H, 4.95; N, 4.91; Found: C, 58.63; H, 5.16; N, 4.93.

Ethyl 3-chloro-2-(trifluoromethyl)benzoate (4z): Reaction was performed on 0.50 mmol scale using 1.5 equiv of 1 at 50° C. for 18 h to give 4z (87.7 mg, 69% yield). Pentane/Ether=5/1 was used for column chromatography. $^1H$ NMR (400 MHz, CDCl$_3$) δ: 7.52 (d, 2H, J=8.0 Hz), 7.50 (dd, 2H, J=8.0, 8.0 Hz), 7.38 (d, 2H, J=8.0 Hz), 4.38 (q, 2H, J=7.2 Hz), 1.36 (t, 3H, J=7.2 Hz). $^{13}C\{^1H\}$ NMR (125 MHz, CDCl$_3$) δ: 167.4, 135.3 (q, $J_{C-F}$=2.5 Hz), 133.6 (q, $J_{C-F}$=1.9 Hz), 133.0, 132.4, 126.5, 125.4 (q, $J_{C-F}$=31.4 Hz), 122.4 (q, $J_{C-F}$=274 Hz), 62.5, 13.8. $^{19}F$ NMR (376 MHz, CDCl$_3$) δ: −58.4. Anal. Calcd for C$_{10}$H$_8$ClF$_3$O$_2$: C, 47.54; H, 3.19; Found: C, 47.65; H, 3.56.

(R)-2,2'-Bis(methoxymethoxy)-3,3'-bis(trifluoromethyl)-1,1'-binaphthyl (4aa; Kobayashi, S.; Ishitani, H. JP2001139508; Wu, T. R.; Shen, L.; Chong. J. M. *Org. Lett.* 2004, 6, 2701.): Reaction was performed on 0.50 mmol scale at 50° C. for 18 h to give 4aa (246.3 mg, 97% yield). Pentane/Ether=5/1 was used for column chromatography. $^1H$ NMR (500 MHz, CDCl$_3$) δ: 8.39 (s, 2H), 8.02 (d, 2H, J=8.0 Hz), 7.55 (dd, 2H, J=7.5, 7.5 Hz), 7.45 (dd, 2H, J=7.5, 7.5 Hz), 7.28 (d, 2H, J=9.0 Hz), 4.81 (d, 2H, J=5.5 Hz), 4.57 (d, 2H, J=5.5 Hz), 2.74, (s, 6H). $^{13}C\{^1H\}$ NMR (125 MHz, CDCl$_3$) δ: 150.8, 135.6, 129.2, 129.1, 129.1, 129.0, 129.0, 128.9 (From 129.2 to 128.9, some peaks were overlapped and C—F coupling constant of the carbon was difficult to analyze), 126.8, 126.2, 126.0, 123.8 (q, $J_{C-F}$=30.1 Hz), 123.6 (q, $J_{C-F}$=271 Hz), 99.7 (q, $J_{C-F}$=1.4 Hz), 56.2. $^{19}$F NMR (469 MHz, CDCl$_3$) δ: −61.2. Anal. Calcd for $C_{26}H_{20}F_6O_4$: C, 61.18; H, 3.95; Found: C, 60.98; H, 3.68.

Example 7

Generation of (phen)Cu—CF$_3$ In Situ and Subsequent Fluoroalkylation Reactions Using Aromatic Iodide (3) as Limiting Agent General Procedure in Glove Box: To a 20-mL vial equipped with a stir bar were added CuCl (99 mg, 1.0 mmol, 2.0 equiv.), KOtBu (112 mg, 1.0 mmol, 2.0 equiv.) and 1,10-phenanthroline (180 mg, 1.0 mmol, 2.0 equiv.), and DMF (2.0 mL) was added. The dark red mixture was stirred at room temperature for 30 min then TMSCF$_3$ (0.148 mL, 1.0 mmol, 2.0 equiv.) was added dropwise. The resulting mixture was further stirred at room temperature for 1 h and then ArI 3 (0.50 mmol) was added. The resulting mixture was stirred at 50° C. for 18 h, then cooled, diluted with Et$_2$O and filtered through a pad of Celite. The Celite pad was washed with Et$_2$O and the combined organic layer was washed with 1M aqueous HCl, saturated aqueous NaHCO$_3$ solution and brine, and dried over Na$_2$SO$_4$. After filtration and evaporation of the solvent, the crude mixture was purified by flash silica gel column chromatography using pentane/Et$_2$O as eluent to give ArCF$_3$ 4.

General Procedure Outside Glove Box: To a 20-mL vial equipped with a stir bar and a Teflon-lined screw cap was added CuCl (99 mg, 1.0 mmol, 2.0 equiv.) then air in the vial was evacuated and dry nitrogen was refilled (once) and were added KOtBu (112 mg, 1.0 mmol, 2.0 equiv.) and 1,10-phenanthroline (180 mg, 1.0 mmol, 2.0 equiv.) then air in the vial was evacuated and dry nitrogen was refilled (twice). To the mixture was added DMF (2.0 mL), and the dark red mixture was stirred at room temperature for 30 min under nitrogen then TMSCF$_3$ (0.148 mL, 1.0 mmol, 2.0 equiv.) was slowly added. The resulting mixture was further stirred at room temperature for 1 h and the stirring was stopped. Then the screw cap was removed and ArI 3 (0.50 mmol) was expeditiously added. While opening the cap, surface of the vial turned green, implying partial decomposition of the copper reagent. The cap of the vial was closed tightly and the vial was evacuated and refilled with dry nitrogen. The resulting mixture was stirred at 50° C. for 18 h, then cooled, diluted with Et$_2$O and filtered through a pad of Celite. The Celite pad was washed with Et$_2$O and the combined organic layer was washed with 1M aqueous HCl, saturated aqueous NaHCO$_3$ solution and brine, and dried over Na$_2$SO$_4$. After filtration and evaporation of the solvent, the crude mixture was purified by flash silica gel column chromatography using pentane/Et$_2$O as eluent to give ArCF$_3$ 4.

Structures and yields for the products are shown in FIG. 3, and experimental details are below.

4-(Trifluoromethyl)biphenyl (4q; Ackermann, L.; Potukuchi, H. K.; Althammer, A.; Born, Robert; Mayer, Peter. Org. Lett. 2010, 12, 1004.): Reaction was performed on 0.50 mmol scale using 1.5 equiv of CuCl, KOtBu, 1,10-phenanthroline and TMSCF$_3$ at 50° C. for 18 h at Glove Box to give 4q (105.3 mg, 95% yield). The same reaction was performed at outside Glove Box using 2.0 equiv of CuCl, KOtBu, 1,10-phenanthroline and TMSCF$_3$ at 50° C. for 18 h to give 4q (99.0 mg, 89% yield). The same reaction was performed at outside Glove Box using 1.5 equiv of CuCl, KOtBu, 1,10-phenanthroline and TMSCF$_3$ at 50° C. for 18 h to give 4q (104.1 mg, 94% yield).

1-(Benzyloxy)-4-(trifluoromethyl)benzene (4r; Pratt, D. A.; de Heer, M. I.; Mulder, P.; Ingold, K. U. J. Am. Chem. Soc. 2001, 123, 5518.): Reaction was performed outside of a Glove Box using 2.0 equiv of CuCl, KOtBu, 1,10-phenanthroline and TMSCF$_3$ at 50° C. for 18 h to give 4r (119.5 mg, 95% yield).

4'-(Trifluoromethyl)acetophenone (4g; Arisawa, M.; Suwa, K.; Yamaguchi, M. Org. Lett. 2009, 11, 625.): Reaction was performed outside of a Glove Box using 2.0 equiv of CuCl, KOtBu, 1,10-phenanthroline and TMSCF$_3$ at 50° C. for 18 h to give 4g (76.0 mg, 79% yield). The same reaction was performed under the same reaction condition with internal standard (p-CF$_3$OC$_6$H$_4$OMe; 1.0 eq) to give 4g (85%, NMR yield).

7-Chloro-4-(trifluoromethyl)quinoline (4x): Reaction was performed outside of a Glove Box using 2.0 equiv of CuCl, KOtBu, 1,10-phenanthroline and TMSCF$_3$ at 50° C. for 18 h to give 4x (106.4 mg, 92% yield).

tert-Butyl 5-(trifluoromethyl)-1H-indole-1-carboxylate (4y): Reaction was performed outside of a Glove Box using 2.0 equiv of CuCl, KOtBu, 1,10-phenanthroline and TMSCF$_3$ at 50° C. for 18 h to give 4y (118.3 mg, 83% yield).

Example 8

Fluoroalkylation Reactions with (phen)Cu— CF$_2$CF$_2$CF$_3$ (2) and Using Aromatic Iodide (3) as Limiting Agent To a 20-mL vial equipped with a stir bar was added ArI 3 (0.50 mmol), 2 (310 mg, 0.75 mmol, 1.5 equiv) and DMF (2.0 mL). And the mixture was stirred at 50° C. After 18 h, the stirring was stopped, and the reaction mixture was diluted with Et$_2$O and filtered through a pad of Celite. The Celite pad was washed with Et$_2$O. The combined filtrate was washed with 1M aqueous HCl, saturated aqueous NaHCO$_3$ solution and brine, and dried over Na$_2$SO$_4$. After filtration and evaporation of the solvent, the crude mixture was purified by flash silica gel column chromatography using pentane/Et$_2$O or pentane as eluent to give ArCF$_2$CF$_2$CF$_3$ 5. Structures and yields for the products 5q, 5r, 5j, 5x and 5y are shown in FIG. 4, and experimental details are below.

4-(Perfluoropropyl)biphenyl (5q; Fialkov, Yu. A.; Shelyazhenko, S. V.; Yagupol'skii, L. M. Zh. Org. Khim. 1983, 19, 1048.): Reaction was performed on 0.50 mmol scale using 1.5 equiv of 2 at 50° C. for 18 h to give 5q (158.9 mg, 99% yield). The same reaction was performed using 1.5 equiv of 2 at rt for 18 h to give 5q (130.5 mg, 81% yield). Pentane was used as eluent for column chromatography. $^1$H NMR (400 MHz, CDCl$_3$) δ: 7.75-7.62 (m, 6H), 7.52-7.42 (m, 3H). $^{13}$C{$^1$H} NMR (125 MHz, CDCl$_3$) δ: 144.9, 139.6, 129.0 (q, $J_{C-F}$=1.63 Hz), 128.3 (q, $J_{C-F}$=1.50 Hz), 127.6-127.3 (m), 118 (tq, $J_{C-F}$=34.3, 286 Hz), 115.4 (tt, $J_{C-F}$=30.9, 254 Hz), 108.8 (tqt (apparently triplet of sextet), $J_{C-F}$=34.3, 30.9, 263 Hz). $^{19}$F NMR (376 MHz, CDCl$_3$) δ: −80.5 (triplet, 3F, J=9.8 Hz), −112 (apparently quartet, 2F, J=9.8 Hz), −127 (apparently singlet, 2F). Anal. Calcd for $C_{15}H_9F_7$: C, 55.91; H, 2.82; Found: C, 55.55; H, 2.62.

1-(Benzyloxy)-4-(perfluoropropyl)benzene (5r): Reaction was performed on 0.50 mmol scale using 1.5 equiv of 2 at 50° C. for 18 h to give 5r (174.7 mg, 99% yield). Pentane was used as eluent for column chromatography. $^1$HNMR (400 MHz, CDCl$_3$) δ: 7.43-7.34 (m, 7H), 7.08-7.06 (m, 2H), 5.11 (s, 2H). $^{13}$C{$^1$H} NMR (125 MHz, CDCl$_3$) δ: 161.5, 136.1, 128.9-127.5 (m, 6C), 120.9 (t, $J_{C-F}$=24.8 Hz), 119.2 (tq, $J_{C-F}$=30.5, 286 Hz), 115.4 (tt, $J_{C-F}$=30.6, 253 Hz), 108.7 (tqt (apparently triplet of sextet), $J_{C-F}$=30.5, 30.6, 265 Hz). $^{19}$F NMR (376 MHz, CDCl$_3$) δ: −80.5 (triplet, 3F, J=8.7 Hz), −111 (apparently quartet, 2F, J=8.7 Hz), −127 (apparently singlet, 2F). Anal. Calcd for C$_{16}$H$_{11}$F$_7$O: C, 54.56; H, 3.15; Found: C, 54.20; H, 3.00.

1-Nitro-4-(perfluoropropyl)benzene (5j): Reaction was performed on 0.50 mmol scale using 1.5 equiv of 2 at 50° C. for 18 h to give 5j (128.4 mg, 88% yield). Pentane was used as eluent for column chromatography. $^1$H NMR (500 MHz, CDCl$_3$) δ: 8.38 (d, 2H, J=9.0 Hz), 7.81 (d, 2H, J=9.0 Hz). $^{13}$C{$^1$H} NMR (125 MHz, CDCl$_3$) δ: 150.2, 134.6 (t, $J_{C-F}$=23.9 Hz), 128.3 (t, $J_{C-F}$=6.3 Hz), 123.9, 117.8 (tq, $J_{C-F}$=33.6, 286 Hz), 114.5 (tt, $J_{C-F}$=31.3, 255 Hz), 108.5 (tqt (apparently triplet of sextet), $J_{C-F}$=33.6, 31.3, 264 Hz). $^{19}$F NMR (469 MHz, CDCl$_3$) δ: −80.4 (triplet, 3F, J=9.4 Hz), −113 (apparently quartet, 2F, J=9.4 Hz), −127 (apparently singlet, 2F). Anal. Calcd for C$_9$H$_4$F$_7$NO$_2$: C, 37.13; H, 1.38; N, 4.81; Found: C, 37.40; H, 1.66; N, 4.86.

7-Chloro-4-(perfluoropropyl)quinoline (5x): Reaction was performed on 0.50 mmol scale using 1.5 equiv of 2 at 50° C. for 18 h to give 5x (150.4 mg, 91% yield). The same reaction was performed using 1.5 equiv of 2 at rt for 18 h to give 5x (152.4 mg, 92% yield). In this substrate, different quenching method was used. After stirring 18 h, the mixture was poured into 29% aqueous ammonium hydroxide solution (20 mL) and extracted with ether (20 mL×3). Then, organic phase was combined and dried over anhydrous NaSO$_4$ and filtrate and evaporate. The resultant was diluted with ether and wash 1 M HCl, sat. NaHCO$_3$ and brine, then dried over Na$_2$SO$_4$. After filtration and evaporation of the solvent, the crude mixture was purified by flash silica gel column chromatography using pentane/Et$_2$O=5/1 to 2/1 as eluent to give ArCF$_3$ 5x. $^1$H NMR (500 MHz, CDCl$_3$) δ: 9.06 (d, 1H, J=4.0 Hz), 8.21 (d, 1H, J=2.0 Hz), 8.09 (dd, 1H, J=2.0, 9.0 Hz), 7.64-7.59 (m, 2H). $^{13}$C{$^1$H} NMR (125 MHz, CDCl$_3$) δ: 150.3, 149.6, 136.3, 133.3 (t, $J_{C-F}$=23.0 Hz), 129.5, 129.4, 125.9 (septet, $J_{C-F}$=10.8 Hz), 122.5, 120.9 (t, $J_{C-F}$=31.4 Hz), 117.8 (tq, $J_{C-F}$=33.6, 286 Hz), 115.9 (tt, $J_{C-F}$=32.9, 260 Hz), 108.9 (tqt (apparently triplet of sextet), $J_{C-F}$=33.6, 32.9, 264 Hz). $^{19}$F NMR (469 MHz, CDCl$_3$) δ: −80.4 (triplet, 3F, J=9.85), −108 (apparently quartet, 2F, J=9.85). −125 (apparently singlet, 2F). Anal. Calcd for C$_{12}$H$_5$ClF$_7$N: C, 43.46; H, 1.52; N, 4.22; Found: C, 43.58; H, 1.79; N, 4.17.

tert-Butyl 5-(perfluoropropyl)-1H-indole-1-carboxylate (5y): Reaction was performed on 0.50 mmol scale using 1.5 equiv of 2 at 50° C. for 18 h to give 5y (177.5 mg, 92% yield). Pentane was used for column chromatography. $^1$H NMR (500 MHz, CDCl$_3$) δ: 8.27 (d, 1H, J=8.5 Hz), 7.81 (s, 1H), 7.70 (d, 1H, J=3.5 Hz), 7.51 (d, 1H, J=8.5 Hz), 6.66 (d, 1H, J=3.5 Hz), 1.69 (s, 9H). $^{13}$C{$^1$H} NMR (125 MHz, CDCl$_3$) δ: 149.3, 136.9, 130.3, 127.5, 122.8 (t, $J_{C-F}$=24.1 Hz), 122.2 (t, $J_{C-F}$=6.3 Hz), 120.0 (t, $J_{C-F}$=6.9 Hz), 118.1 (tq, $J_{C-F}$=34.1, 286 Hz), 115.7 (tt, $J_{C-F}$=30.4, 254 Hz), 115.3, 108.8 (tqt (apparently triplet of sextet), $J_{C-F}$=34.1, 30.4, 262 Hz), 107.3, 84.5, 28.1. $^{19}$F NMR (469 MHz, CDCl$_3$) δ: −80.5 (triplet, 3F, J=9.4 Hz), −113 (apparently quartet, 2F, J=9.4 Hz), −127 (apparently singlet, 2F). HRMS (EI): Calcd for C$_9$H$_4$F$_7$NO$_2$: 385.0913; Found: 385.0930.

4-(n-Butyl)-1-(perfluoropropyl)benzene (5b): To a 4-mL vial equipped with a stir bar were added (1,10-phenanthroline)(heptafluoropropyl)copper(I) (2) (14.4 mg, 0.035 mmol) and 4-(trifluoromethoxy)anisole in DMF (0.70 mL, 0.050 M, 0.035 mmol). To the mixture was added ArI 3b (31 μL, 0.18 mmol, 5.0 equiv), and the mixture was stirred at room temperature for 18 h. After the reaction, the mixture was transferred to an NMR tube, and the yield of ArCF$_2$CF$_2$CF$_3$ 5b was determined by $^{19}$F NMR analysis to be 84%.

Example 9

Generation of (phen)Cu—CF$_2$CF$_2$CF$_3$ In Situ and Subsequent Fluoroalkylation Reactions Using Aromatic Iodide (3) as Limiting Agent General Procedure in Glove Box: To a 20-mL vial equipped with a stir bar were added CuCl (99 mg, 1.0 mmol, 2.0 equiv.), KOtBu (112 mg, 1.0 mmol, 2.0 equiv.) and 1,10-phenanthroline (180 mg, 1.0 mmol, 2.0 equiv.), and DMF (2.0 mL) was added. The dark red mixture was stirred at room temperature for 30 min then TMSCF$_2$CF$_2$CF$_3$ (0.203 mL, 1.0 mmol, 2.0 equiv.) was added dropwise. The resulting mixture was further stirred at room temperature for 1 h and then ArI 3q (0.50 mmol) was added. The resulting mixture was stirred at 80° C. for 18 h, then cooled, diluted with Et$_2$O and filtered through a pad of Celite. The Celite pad was washed with Et$_2$O and the combined organic layer was washed with 1M aqueous HCl, saturated aqueous NaHCO$_3$ solution and brine, and dried over Na$_2$SO$_4$. After filtration and evaporation of the solvent, the crude mixture was purified by flash silica gel column chromatography using pentane/Et$_2$O as eluent to give ArCF$_2$CF$_2$CF$_3$ 5q.

General Procedure for Conducting Reactions Outside of a Glove Box: To a 20-mL vial equipped with a stir bar and a Teflon-lined screw cap was added CuCl (99 mg, 1.0 mmol, 2.0 equiv.) then air in the vial was evacuated and dry nitrogen was refilled (once) and were added KOtBu (112 mg, 1.0 mmol, 2.0 equiv.) and 1,10-phenanthroline (180 mg, 1.0 mmol, 2.0 equiv.) then air in the vial was evacuated and dry nitrogen was refilled (twice). To the mixture was added DMF (2.0 ml), and the dark red mixture was stirred at room temperature for 30 min under nitrogen then TMSCF$_2$CF$_2$CF$_3$ (0.2013 mL, 1.0 mmol, 2.0 equiv.) was slowly added. The resulting mixture was further stirred at room temperature for 1 h and the stirring was stopped. Then the screw cap was removed and ArI 3q (0.50 mmol) was expeditiously added. While opening the cap, surface of the vial turned green, implying partial decomposition of the copper reagent. The cap of the vial was closed tightly and the vial was evacuated and refilled with dry nitrogen. The resulting mixture was stirred at 80° C. for 18 h, then cooled, diluted with Et$_2$O and filtered through a pad of Celite. The Celite pad was washed with Et$_2$O and the combined organic layer was washed with 1M aqueous HCl, saturated aqueous NaHCO$_3$ solution and brine, and dried over Na$_2$SO$_4$. After filtration and evaporation of the solvent, the crude mixture was purified by flash silica gel column chromatography using pentane/Et$_2$O as eluent to give ArCF$_2$CF$_2$CF$_3$ 5q.

4-(Perfluoropropyl)biphenyl (5q): Reaction was performed on 0.50 mmol scale using 2.0 equiv of CuCl, KOtBu, 1,10-phenanthroline and TMSCF$_3$ at 50° C. or 80° C. for 18 h in Glove Box to give 5q (50° C.: 92.3 mg, 57% yield 80° C.: 130.1 mg, 81% yield). The same reaction was performed at outside Glove Box using 2.0 equiv of CuCl, KOtBu, 1,10-phenanthroline and TMSCF$_3$ at 80° C. for 18 h to give 5q (127.6 mg, 79% yield).

Example 10

Mechanistic Studies of Fluoroalkylation Reaction

To assess whether the reaction proceeds via radical intermediates, the trifluoromethylation reaction was conducted with 2-(allyloxy)iodobenzene 3ab. If the trifluoromethylation occurs through an aryl radical, then cyclized product 6 should be observed (FIG. 5). Instead, the trifluoromethylarene 4ab was obtained in 91% yield, and the cyclized product 6 was not detected by GC-MS analysis. This result implies that the copper-mediated trifluoromethylation reaction proceeds through a non-radical pathway.

To a 4-mL vial equipped with a stir bar were added (1,10-phenanthroline)(trifluoromethyl)copper(I) (1) (10.9 mg, 0.035 mmol) and 4-(trifluoromethoxy)anisole in DMF (0.70 mL, 0.050 M, 0.035 mmol). To the mixture was added 2-(allyloxy)iodobenzene 3ab (45.5 mg, 0.175 mmol, 5.0 equiv), and the mixture was stirred at room temperature for 18 h. After the reaction, the mixture was transferred to an NMR tube, and the yield of 2-(allyloxy)(trifluoromethyl)benzene 4ab was determined by $^{19}$F NMR analysis to be 91%. The mixture was also analyzed by GC-MS. Only 4ab (12.304 min; m/z=202) was observed and no cyclized byproduct 6 (11.902 min; m/z=134) was detected.

Example 11

Fluoroalkylation Reactions of Aromatic Bromides (7) Using (phen)Cu—CF$_3$ (1) as Limiting Agent To a 4-mL vial equipped with a stir bar were added 1 (10.9 mg, 0.035 mmol), ArBr 7 (if solid, 0.175 mmol, 5.0 equiv) and 4-(trifluoromethoxy)anisole (internal standard for $^{19}$F NMR analysis) in DMF (0.70 mL, 0.050 M, 0.035 mmol). To the mixture was added ArBr 7 (if liquid, 0.175 mmol, 5.0 equiv), and the mixture was stirred at 110° C. After 18 h, the stirring was stopped and cooled to room temperature, and the reaction mixture was transferred to an NMR tube, and the yield of the product 8 was measured by $^{19}$F NMR analysis with the following parameters after reduction of the sw (sweep width) to include both standard (−58.6 ppm) and product peaks: at=10 (s), d1=10 (s), pw90=15.5 (ms), pw=15.5 (ms) and nt=4. Structures and yields for products 8j, 8a, 8q, 8c, 8g, 8t, 8h, 8i and 8ac are shown in FIG. 6.

Example 12

Fluoroalkylation Reaction of Vinyl Halide Using (phen)Cu—CF$_3$ (1) as Limiting Agent To a 4-mL vial equipped with a stir bar were added 1 (10.9 mg, 0.035 mmol) and 4-(trifluoromethoxy)-anisole (internal standard for $^{19}$F NMR analysis) in DMF (0.70 mL, 0.050 M, 0.035 mmol). To this mixture was added (E)-n-Hexyl-CH=CHI (0.35 mmol, 10.0 equiv), and a precipitate formed immediately. The mixture was stirred at room temperature. After 18 h, the stirring was stopped, and the reaction mixture was transferred to an NMR tube, and the yield of the product was measured by $^{19}$F NMR analysis with the following parameters after reduction of the sw (sweep width) to include both standard (−58.6 ppm) and product peaks: at=10 (s), d1=10 (s), pw90=15.5 (µs), pw=15.5 (µs) and nt=4. Yield of (E)-n-Hexyl-CH=CH(CF$_3$) was 99%.

Example 13

Formation of (1,10-Phenanthroline)(trifluoromethyl)copper(I) (1)

Copper mesityl was prepared according to Tsuda et al, *J. Org. Chem.* 1981, 46, 192) as a dull yellow powder, and was dissolved in THF (0.3 M) to give a light yellow solution. To this solution, 1.0 equivalent of anhydrous t-BuOH was added dropwise, and the resulting light yellow solution was stirred at room temperature for 2 hours. 1,10-Phenanthroline was dissolved in THF (0.3 M), and the resulting clear solution was added to the copper-containing mixture to give a very dark purple solution (0.15 M overall). If the copper mesityl had insufficient purity, a dark solid precipitated, which would require the reaction to be repeated with higher quality copper mesityl.

After stirring this dark solution for 30 minutes, TMSCF$_3$ was added slowly with rapid stirring. A light brown/orange solid started to precipitate during or shortly after the addition of TMSCF$_3$. The resulting suspension was stirred at room temperature for 12 hours. The solid was collected, washed with ether until the eluent was clear, and dried to provide reagent 1. Reagent 1 was obtained as an air and moisture-sensitive orange solid in 80-85% yield, and its characterization data was consistent with that of complex 1 of Example 1.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A composition, consisting essentially of:
   copper,
   a fluoroalkyl group bonded to the copper through a carbon-copper bond, and
   a ligand comprising at least one group-V donor;
   wherein the molar ratio of copper to the fluoroalkyl group is approximately 1, and
   wherein the ligand is 1,10-phenanthroline and the fluoroalkyl group is —CF$_3$, —CF$_2$CF$_2$CF$_3$, or —CF$_2$CF$_3$.

2. A composition, consisting essentially of:
   copper,
   a fluoroalkyl group bonded to the copper through a carbon-copper bond,
   a first ligand comprising at least one group-V donor, and
   a second ligand, different from the first ligand;
   wherein the molar ratio of copper to the fluoroalkyl group is approximately 1.

3. The composition of claim 2, wherein the second ligand comprises at least one of a group-V donor and a group-VI donor.

4. The composition of claim 2, wherein the second ligand is selected from the group consisting of a phenanthroline, an N,N'-disubstituted diamine, a bipyridine, a pyridine, a trialkylamine, an azole, a phosphine, a phosphite, an ether, an amide and a sulfide.

5. The composition of claim 2, wherein the second ligand is selected from the group consisting of 1,10-phenanthroline (phen), bipyridyl (bipy), pyridyl (Py), tetramethylenediamine (TMEDA), N,N'-dimethylethylenediamine (DMEDA), N,N'-dimethyl-cyclohexanediamine (DMECA), tributyl phosphine [(n-Bu)$_3$P], triphenyl phosphine (Ph$_3$P), trimethyl phosphite [(MeO)$_3$P], triphenyl phosphite [(PhO)$_3$P], N-methylimidazole, oxazole, N-methyl pyrazole, triethylamine, diethyl ether, THF, DMF, urea, dimethyl sulfide, thiourea, acetate (OAc) and pivalate.

6. The composition of claim 2, wherein
   the first ligand is 1,10-phenanthroline,
   the fluoroalkyl group is selected from the group consisting of —CF$_3$ and —CF$_2$CF$_2$CF$_3$, and the second ligand is selected from the group consisting of bipyridyl (bipy), pyridyl (Py), tetramethylenediamine (TMEDA),
N,N'-dimethylethylenediamine (DMEDA), N,N'-dimethyl-cyclohexanediamine (DMECA), tributyl phosphine [(n-Bu)$_3$P], triphenyl phosphine (Ph$_3$P), trimethyl phosphite [(MeO)$_3$P], triphenyl phosphite [(PhO)$_3$P], N-methylimidazole, oxazole, N-methyl pyrazole, triethylamine, diethyl ether, THF, DMF, urea, dimethyl sulfide, thiourea, acetate (OAc), and pivalate.

7. The composition of claim 2, wherein
the first ligand is 1,10-phenanthroline,
the fluoroalkyl group is —CF$_2$CF$_3$, and
the second ligand is selected from the group consisting of bipyridyl (bipy), pyridyl (Py), tetramethylenediamine (TMEDA),
N,N'-dimethylethylenediamine (DMEDA), N,N'-dimethyl-cyclohexanediamine (DMECA), tributyl phosphine [(n-Bu)$_3$P], triphenyl phosphine (Ph$_3$P), trimethyl phosphite [(MeO)$_3$P], triphenyl phosphite [(PhO)$_3$P], N-methylimidazole, oxazole, N-methyl pyrazole, triethylamine, diethyl ether, THF, DMF, urea, dimethyl sulfide, thiourea, acetate (OAc), and pivalate.

* * * * *